(12) United States Patent
Ishikawa et al.

(10) Patent No.: US 7,778,843 B2
(45) Date of Patent: Aug. 17, 2010

(54) APPARATUS FOR CALCULATING NUTRIENT REQUIREMENT AMOUNT, AN APPARATUS FOR SUGGESTING A NUTRITIONAL SUPPLEMENT, AN APPARATUS FOR SUGGESTING A NUTRITIONAL SUPPLEMENT, A BLENDING APPARATUS OF A NUTRITIONAL SUPPLEMENT AND A BLENDING SYSTEM OF A NUTRITIONAL SUPPLEMENT

(75) Inventors: Masahito Ishikawa, Tokyo (JP); Kayo Sano, Tokyo (JP)

(73) Assignee: Nutrition Act. Co., Ltd., Tokyo (JP)

( * ) Notice: Subject to any disclaimer, the term of this patent is extended or adjusted under 35 U.S.C. 154(b) by 2000 days.

(21) Appl. No.: 10/745,741

(22) Filed: Dec. 23, 2003

(65) Prior Publication Data
US 2004/0138926 A1    Jul. 15, 2004

Related U.S. Application Data

(63) Continuation of application No. PCT/JP01/05624, filed on Jun. 29, 2001.

(51) Int. Cl.
G06Q 10/00    (2006.01)
(52) U.S. Cl. .......................................... 705/2
(58) Field of Classification Search .................. None
See application file for complete search history.

(56) References Cited

FOREIGN PATENT DOCUMENTS

| JP | 05-128921 | 5/1993 |
|---|---|---|
| JP | 05-287483 | 11/1993 |
| JP | 07-064963 | 3/1995 |
| JP | 09-101946 | 4/1997 |
| JP | 2000-20589 | 1/2000 |
| JP | 2000-158853 | 6/2000 |
| JP | 2001-101157 | 4/2001 |

OTHER PUBLICATIONS

English Translation of International Preliminary Examination Report.
International Preliminary Examination Report (PCT/IPEA/409).
International Search Report (PCT/ISA/210).

*Primary Examiner*—Luke Gilligan
*Assistant Examiner*—Valerie Lubin
(74) *Attorney, Agent, or Firm*—Nutter McClennen & Fish LLP; John J. Penny, V

(57) ABSTRACT

It is provided with a medical inquiry processing unit for acquiring the response to a medical inquiry presenting medical inquiry items to a person to be examined, a nutrient requirement amount calculating unit for calculating the nutrient requirement amount of the person to be examined from the response to the medical inquiry, a nutritional supplement suggesting unit for suggesting the blend of a nutritional supplement based on the nutrient requirement amount of the person to be examined and a nutritional supplement blending unit for blending nutrients to prepare the nutritional supplement based on the blend of the nutritional supplement.

8 Claims, 22 Drawing Sheets

| CUSTOMER ID | NAME | DATE OF BIRTH | SEX | ADDRESS | ADDRESS OF WORKPLACE | LIFE GOAL | PREFERENCE FOR NUTRITIONAL SUPPLEMENT | | | | STEP |
|---|---|---|---|---|---|---|---|---|---|---|---|
| | | | | | | | COLOR | TASTE | SMELL | PACKAGE | |
| 001 | ○○○○ | 1975.1.1 | FEMALE | @@@ SAITAMA-KEN | ### SHINJUKU-KU TOKYO | ... | 1 | 1 | 1 | 2 | 3 |

| MEDICAL INQUIRY ID | MEDICAL INQUIRY MESSAGE | BRANCHING DESTINATION FOR RESPONSE | | | FOR STEP | FOR LIFE GOAL | MEDICAL INQUIRY INTERVAL | FOR INSUFFICIENT NUTRIENT |
|---|---|---|---|---|---|---|---|---|
| | | Y | NY | N | 1 2 3 4 5 | 1 2 3 | | 1 2 ... 20 21 |
| 1000 | ARE YOU AFFECTED BY AIR POLLUTION? | 0 | 0 | 0 | ✓ ✓ | ✓ ✓ ✓ | ONE WEEK | |
| 1003 | WHAT'S YOUR HEIGHT? [NUMERICAL VALUE] | 0 | 0 | 0 | ✓ ✓ ✓ ✓ ✓ | ✓ ✓ ✓ | ONE YEAR | |
| 1004 | WHAT'S YOUR WEIGHT? [NUMERICAL VALUE] | 0 | 0 | 0 | ✓ ✓ ✓ ✓ ✓ | ✓ ✓ ✓ | TWO WEEKS | |
| 2000 | DO YOU HAVE MEALS OF 30 FOOD ITEMS A DAY? | 0 | 2100 | 2100 | ✓ ✓ ✓ ✓ ✓ | ✓ ✓ ✓ | EVERY TIME | |
| 2002 | DO YOU HAVE WELL-BALANCED MEALS WITH 6 FOOD GROUPS? | 3000 | 3000 | 3000 | ✓ ✓ ✓ ✓ ✓ | ✓ ✓ ✓ | ONE WEEK | |
| 2003 | DO YOU HAVE MEALS WITH EXCESSIVE SALT? | 0 | 0 | 0 | ✓ ✓ ✓ ✓ ✓ | ✓ ✓ ✓ | ONE WEEK | |
| 2100 | IS YOUR STAPLE FOOD BALANCED? | 0 | 0 | 0 | ✓ ✓ ✓ ✓ ✓ | ✓ ✓ ✓ | ONE WEEK | |
| 2104 | DO YOU DRINK MILK OFTEN? | 0 | 0 | 4000 | ✓ ✓ ✓ ✓ ✓ | ✓ ✓ ✓ | ONE WEEK | |
| 3000 | DO YOU HAVE A SYMPTOM THAT YOU GET TIRED EASILY OR FEEL HEAVY? | 0 | 0 | 0 | ✓ ✓ ✓ ✓ ✓ | ✓ ✓ ✓ | ONE WEEK | |
| 3100 | DO YOU FEEL HEAVY IN YOUR ARMS AND LEGS? | 0 | 0 | 0 | ✓ ✓ ✓ ✓ ✓ | ✓ ✓ ✓ | ONE WEEK | |
| 3108 | ARE YOU LIABLE TO SUFFER FROM SUMMER HEAT? | 0 | 0 | 0 | ✓ ✓ ✓ ✓ ✓ | ✓ ✓ ✓ | THREE MONTHS | |
| 3109 | DO YOU FEEL DIZZY? | 0 | 0 | 0 | ✓ ✓ ✓ ✓ ✓ | ✓ ✓ ✓ | ONE WEEK | |
| 4000 | HAVE YOU TAKEN IN THE PREVIOUS NUTRITIONAL SUPPLEMENT? | 9999 | 9999 | 9999 | ✓ ✓ ✓ ✓ ✓ | ✓ ✓ ✓ | EVERY TIME | |

| CUSTOMER ID | REGISTRATION DATE | KIND OF HISTORY | MEDICAL INQUIRY OR NUTRIENT ID | MEDICAL INQUIRY ID | RESPONSE TO MEDICAL INQUIRY OR NUTRIENT REQUIREMENT AMOUNT |
|---|---|---|---|---|---|
| 001 | 1999.1.1 | MEDICAL INQUIRY | 1000 | | Y |
| 001 | 1999.1.1 | MEDICAL INQUIRY | 1001 | | NY |
| 001 | 1999.1.1 | INSUFFICIENT DEGREE | 1 | | 2400IU |
| 001 | 1999.1.1 | PREPARATION | 1 | | 1800UI |

FIG. 6

| ADDRESS | MEDICAL INQUIRY ID | RESPONSE TO MEDICAL INQUIRY |
|---|---|---|
| SHINJUKU-KU TOKYO | 1000 | Y |
| SAITAMA-KEN | 1000 | NY |
| | | |
| | | |

*FIG. 7*

| MEDICAL INQUIRY ID | INSUFFICIENT NUTRIENT | | | | |
|---|---|---|---|---|---|
| | 1 | 2 | ... | 20 | 21 |
| 1000 | 30% | 0% | | 0% | 0% |
| 1003 | 0% | 0% | | 0% | 0% |
| 1004 | 0% | 0% | | 0% | 0% |
| 2000 | 15% | 15% | | 15% | 15% |
| 3109 | 0% | 0% | | 30% | 0% |
| 4000 | 0% | 0% | | 0% | 0% |

FIG. 8

| SEX | AGE | NUTRIENT ID | REQUIRED AMOUNT | UPPER LIMIT INGESTION AMOUNT |
|---|---|---|---|---|
| FEMALE | 18~29 | 1 | 1800IU | 5000IU |
| FEMALE | 18~29 | 2 | 100IU | 2000IU |
|  |  |  |  |  |
|  |  |  |  |  |
| FEMALE | 18~29 | 20 | 600mg | 2500mg |
| FEMALE | 18~29 | 21 | 250mg | 700mg |
|  |  |  |  |  |
|  |  |  |  |  |

FIG. 9

| LIFE GOAL ID | NUTRIENT FOR PURPOSE | | | | |
|---|---|---|---|---|---|
| | 1 | 2 | ... | 20 | 21 |
| 1 | 0% | 0% | | 0% | 0% |
| 2 | 150% | 0% | | 0% | 0% |
| 3 | 100% | 0% | | 100% | 100% |

| PRESUMPTION CONDITION | | PRESUMED DISEASE NAME | MEDICAL DEPARTMENT |
|---|---|---|---|
| RESPONSE TO MEDICAL INQUIRY | NUTRITIONAL CONDITION | | |
| MEDICAL INQUIRY ID = 3109 → Y AND MEDICAL INQUIRY ID = 4000 → Y | 5 (VITAMIN B1) 6 (VITAMIN B2) 7 (NIACIN) 8 (PANTOTHENIC ACID) 15 (IRON) ARE SUFFICIENT | VERTIGO | OTORHINOLOGY NEUROSURGERY |

| NAME OF MEDICAL INSTITUTION | MEDICAL DEPARTMENT | ADDRESS | CONTACT PLACE (DESTINATION) |
|---|---|---|---|
| ○○ HOSPITAL | OTORHINOLOGY, OPHTHALMOLOGY | @@@ SAITAMA-KEN | XXX-XXX-XXXX |
| | | | |
| | | | |

| CORRELATION ID | CONDITION | INSUFFICIENT NUTRIENT (PRESUMED) | | | | |
|---|---|---|---|---|---|---|
| | | 1 | 2 | ... | 20 | 21 |
| 001 | ADDRESS OF WORKPLACE = "TOKYO" | ∨ | | | ∨ | ∨ |

APPARATUS FOR CALCULATING NUTRIENT REQUIREMENT AMOUNT, AN APPARATUS FOR SUGGESTING A NUTRITIONAL SUPPLEMENT, AN APPARATUS FOR SUGGESTING A NUTRITIONAL SUPPLEMENT, A BLENDING APPARATUS OF A NUTRITIONAL SUPPLEMENT AND A BLENDING SYSTEM OF A NUTRITIONAL SUPPLEMENT

The present application is a continuation application of PCT/JP01/05624 filed on Jun. 29, 2001, the contents of which are incorporated herein by reference.

BACKGROUND OF THE INVENTION

1. Field of the Invention

The present invention relates to an apparatus for calculating nutrient requirement amount, an apparatus for suggesting a nutritional supplement, a blending apparatus of a nutritional supplement and a blending system of a nutritional supplement.

2. Related Art

The art of performing nutritional guidance through examining the nutritional condition of a person to be examined is disclosed in, e.g., Japanese Patent Applications Publication No. 2001-101157 and 2000-158853.

The application Publication No. 2001-101157 provides a device and a system that suggest information about a recipe for a meal to a person to be examined by using the nutritive value and the necessary nutritive value.

The application Publication No. 2000-158853 provides an apparatus and a system that inform a person to be examined whether a latent trace nutrient deficiency disease exists for nutritional guidance by evaluating the medical inquiry result of eating habits and health conditions and summarizing the result of the evaluation.

The reason why the person to be examined aims to improve his or her nutritional condition is not only to fill his or herself with necessary nutrients merely but to achieve his or her various life goals such as beauty, health, diet and the like.

Conventionally, it was difficult to support the nutritional ingestion corresponding to the constitution or the life goal of each of the people examined.

SUMMARY OF THE INVENTION

Accordingly, it is an object of the present invention to overcome the above drawbacks accompanying the conventional art. The above and other objects can be achieved by blends described in the independent claims. The dependent claims define further advantageous and exemplary blends of the present invention.

In order to solve the problems above, according to the first aspect of the present invention, an apparatus for calculating nutrient requirement amount of a person to be examined from a response to a medical inquiry, includes a medical inquiry response acquiring unit for acquiring a plurality of responses to the medical inquiry from the person to be examined at a different time or on a different day, an insufficient nutrient processing unit for determining an insufficient degree of nutrient corresponding to each response to the medical inquiry acquired by the medical inquiry response acquiring unit and a nutrient requirement amount calculating unit for calculating the nutrient requirement amount of the person to be examined based on a result of accumulating the insufficient degree of nutrient.

The apparatus for calculating nutrient requirement amount may further include a medical inquiry processing unit for selecting a medical inquiry item for the person to be examined from a medical inquiry item database based on change in the nutrient requirement amount of the person to be examined caused by passage of time, during the medical inquiry except a first time.

The apparatus for calculating nutrient requirement amount may further include a medical inquiry processing unit for selecting a medical inquiry item for the person to be examined from a medical inquiry item database based on a life goal predetermined by the person to be examined, during the medical inquiry except a first time.

The apparatus for calculating nutrient requirement amount may further include a medical inquiry processing unit for selecting a medical inquiry item for the person to be examined from a medical inquiry item database based on a time interval predetermined for each medical inquiry item, during the medical inquiry except a first time.

The apparatus for calculating nutrient requirement amount may further include a medical inquiry processing unit for displaying a medical inquiry item in an order, wherein a necessity degree of response is from high to low, to a terminal with which the person to be examined inputs the response to the medical inquiry, during the medical inquiry except a first time.

The apparatus for calculating nutrient requirement amount may further include a medical inquiry history database for storing a history of the nutrient requirement amount of the person to be examined and a medical inquiry processing unit for selecting a medical inquiry item for the person to be examined from a medical inquiry item database by using the history of the person to be examined, during the medical inquiry except a first time.

The apparatus for calculating nutrient requirement amount may further include a medical inquiry processing unit for selecting a medical inquiry item to perform the medical inquiry on the person to be examined, wherein the nutrient requirement amount calculating unit may output advice about nutrient ingestion to the person to be examined based on the nutrient requirement amount of the person to be examined, the medical inquiry processing unit may designate the medical inquiry item to inquire about a nutrient ingestion condition indicating whether the person to be examined is taking in the nutrient requirement amount outputted by the nutrient requirement amount calculating unit at a previous time and the nutrient requirement amount calculating unit may calculate the nutrient requirement amount of the person to be examined based on a response to a medical inquiry about the nutrient ingestion condition.

The nutrient requirement amount calculating unit may output medical treatment recommendation information to recommend medical treatment at a medical institution, in case of judging that the person to be examined is taking in the nutrient based on the nutrient requirement amount and the nutrient requirement amount of the person to be examined is not improved in regard to at least one of the nutrients, as a result of the medical inquiry about the nutrient ingestion condition.

The nutrient requirement amount calculating unit may further include a disease name presuming unit for judging a presumed disease name based on a result of calculating the nutrient requirement amount of the person to be examined, and outputs the presumed disease name as the medical treatment recommendation information.

The nutrient requirement amount calculating unit may further include a disease name presuming unit for judging a presumed disease name based on a result of calculating the nutrient requirement amount and a medical institution recommending unit for selecting a recommended medical institution corresponding to the presumed disease name, and may output the recommended medical institution as the medical treatment recommendation information.

According to the second aspect of the present invention, an apparatus for calculating nutrient requirement amount of a person to be examined from a response to a medical inquiry, includes a medical inquiry response acquiring unit for acquiring the response to the medical inquiry of a medical inquiry item from the person to be examined, an insufficient nutrient processing unit for determining an insufficient degree of nutrient corresponding to each response to the medical inquiry acquired by the medical inquiry response acquiring unit and a nutrient requirement amount calculating unit for calculating the nutrient requirement amount of the person to be examined based on living environment information indicating a living environment of the person to be examined acquired from an outer part and a result of accumulating the insufficient degree of nutrient.

The nutrient requirement amount calculating unit may further include a living environment database for storing the living environment information corresponding to each region and a living environment searching unit for acquiring the living environment information corresponding to an address of the person to be examined by searching the living environment database by using the address predetermined by the person to be examined, and may calculate the nutrient requirement amount of the person to be examined by using the living environment information searched by the living environment searching unit.

The nutrient requirement amount calculating unit may further include a living environment database for storing the living environment information corresponding to each region, a living environment searching unit for acquiring the living environment information corresponding to an address of the person to be examined by searching the living environment database by using the address predetermined by the person to be examined and a workplace living environment searching unit for acquiring living environment information corresponding to an address of a workplace of the person to be examined by searching the living environment database by using the address of the workplace predetermined by the person to be examined, and may calculate the nutrient requirement amount of the person to be examined by using the living environment information corresponding to the address and the address of the workplace.

According to the third aspect of the present invention, an apparatus for calculating nutrient requirement amount of a person to be examined from a response to a medical inquiry, includes a medical inquiry response acquiring unit for acquiring the response to the medical inquiry of a medical inquiry item from the person to be examined, an insufficient nutrient processing unit for determining an insufficient degree of nutrient corresponding to each response to the medical inquiry acquired by the medical inquiry response acquiring unit and a nutrient requirement amount calculating unit for calculating the nutrient requirement amount of the person to be examined based on a result of accumulating the insufficient degree of nutrient, wherein the nutrient requirement amount calculating unit includes a restriction processing unit for adjusting the nutrient requirement amount based on predetermined restriction information about the nutrient requirement amount.

The nutrient requirement amount calculating unit may further include a nutrient-for-purpose processing unit for adjusting the nutrient requirement amount based on a life goal of the person to be examined acquired from an outer part.

The nutrient requirement amount calculating unit may reduce the insufficient degree of nutrient, which results from accumulation corresponding to each response to the medical inquiry, in comparison to a first time in regard to at least one of responses to the medical inquiry, during the medical inquiry except the first time.

The nutrient requirement amount calculating unit may further include an interaction processing unit for adjusting the nutrient requirement amount based on predetermined information about interaction of nutrients.

According to the fourth aspect of the present invention, an apparatus for calculating nutrient requirement amount of a person to be examined from a response to a medical inquiry, includes a nutrient requirement amount calculating unit for acquiring the response of the person to be examined to the medical inquiry of a medical inquiry item from an outer part and calculating the nutrient requirement amount of the person to be examined based on a result of accumulating insufficient nutrients corresponding to each response to the medical inquiry, a correlation processing unit for analyzing a correlation between the nutrient requirement amount judged by the nutrient requirement amount calculating unit and a living environment acquired from an outer part, in regard to a plurality of people to be examined and a medical inquiry processing unit for designating the medical inquiry item to perform the medical inquiry on the person to be examined by using a result of the analysis of the correlation.

According to the fifth aspect of the present invention, an apparatus for calculating nutrient requirement amount of a person to be examined from a response to a medical inquiry, includes a nutrient requirement amount calculating unit for acquiring the response of the person to be examined to the medical inquiry of a medical inquiry item from an outer part and calculating the nutrient requirement amount of the person to be examined based on a result of accumulating insufficient nutrients corresponding to each response to the medical inquiry, a correlation processing unit for analyzing a correlation between the nutrient requirement amount calculated by the nutrient requirement amount calculating unit and a life goal acquired from an outer part, in regard to a plurality of people to be examined and a medical inquiry processing unit for designating a medical inquiry item to perform the medical inquiry on the person to be examined by using a result of the analysis of the correlation.

According to the sixth aspect of the present invention, an apparatus for suggesting a blend of a nutritional supplement by calculating nutrient requirement amount of a person to be examined from a response to a medical inquiry, includes a nutrient requirement amount calculating unit for calculating the nutrient requirement amount of the person to be examined by acquiring the response of the person to be examined to the medical inquiry of a medical inquiry item and a nutritional supplement suggesting unit for suggesting the blend of the nutritional supplement based on information about the nutrient requirement amount of the person to be examined calculated by the nutrient requirement amount calculating unit.

The nutrient requirement amount calculating unit may calculate the nutrient requirement amount of the person to be examined based on the response of the person to be examined to the medical inquiry acquired from a plurality of outer parts at a different time or on a different day.

The apparatus for suggesting a blend of a nutritional supplement may further include a medical inquiry processing unit for selecting the medical inquiry item for the person to be examined from a medical inquiry item database based on change in the nutrient requirement amount of the person to be examined caused by passage of time, during the medical inquiry except a first time.

The apparatus for suggesting a blend of a nutritional supplement may further include a medical inquiry processing unit for selecting the medical inquiry item for the person to be examined from a medical inquiry item database based on a life goal predetermined by the person to be examined, during the medical inquiry except a first time.

The apparatus for suggesting a blend of a nutritional supplement may further include a medical inquiry processing unit for selecting the medical inquiry item for the person to be examined from a medical inquiry item database based on a time interval predetermined for each medical inquiry item, during the medical inquiry except a first time.

The apparatus for suggesting a blend of a nutritional supplement may further include a medical inquiry processing unit for displaying the medical inquiry item in an order, wherein a necessity degree of response is from high to low, to a terminal with which the person to be examined inputs the response to the medical inquiry, during the medical inquiry except a first time.

The apparatus for suggesting a blend of a nutritional supplement may further include a medical inquiry history database for storing a history of the nutrient requirement amount of the person to be examined and a medical inquiry processing unit for selecting the medical inquiry item for the person to be examined from a medical inquiry item database by using the history of the person to be examined, during the medical inquiry except a first time.

The apparatus for suggesting a blend of a nutritional supplement may further include a medical inquiry processing unit for selecting the medical inquiry item of a nutrient ingestion condition indicating whether the person to be examined is taking in the nutritional supplement suggested by the nutritional supplement blending unit at a previous time, wherein the nutrient requirement amount calculating unit calculates the nutrient requirement amount of the person to be examined based on the response to the medical inquiry about the nutrient ingestion condition.

The nutrient requirement amount calculating unit may output medical treatment recommendation information recommending medical treatment at a medical institution, in case of judging that the person to be examined is taking in the nutritional supplement and the nutrient requirement amount of the person to be examined is not improved in regard to at least one of the nutrients, as a result of the medical inquiry about the nutrient ingestion condition.

The nutrient requirement amount calculating unit may further include a disease name presuming unit for judging a presumed disease name based on a result of calculating the nutrient requirement amount of the person to be examined, and outputs the presumed disease name as the medical treatment recommendation information.

The nutrient requirement amount calculating unit may further include a disease name presuming unit for judging a presumed disease name based on a result of calculating the nutrient requirement amount of the person to be examined and a medical institution recommending unit for selecting a recommended medical institution corresponding to the presumed disease name, and may output the recommended medical institution as the medical treatment recommendation information.

The nutrient requirement amount calculating unit may calculate the nutrient requirement amount of the person to be examined by using living environment information indicating a living environment of the person to be examined from an outer part.

The nutrient requirement amount calculating unit may further include a living environment database for storing the living environment information corresponding to each region and a living environment searching unit for acquiring the living environment information corresponding to an address of the person to be examined by searching the living environment database by using the address predetermined by the person to be examined, and may calculate the nutrient requirement amount of the person to be examined by using the living environment information searched by the living environment searching unit.

The nutrient requirement amount calculating unit may further include a living environment database for storing the living environment information corresponding to each region, a living environment searching unit for acquiring the living environment information corresponding to an address of the person to be examined by searching the living environment database by using the address predetermined by the person to be examined and a workplace living environment searching unit for acquiring living environment information corresponding to an address of a workplace of the person to be examined by searching the living environment database by using the address of the workplace predetermined by the person to be examined, and may calculate the nutrient requirement amount of the person to be examined by using the living environment information corresponding to the address and the address of the workplace.

The nutrient requirement amount calculating unit may calculate the nutrient requirement amount of the person to be examined by using a life goal predetermined by the person to be examined.

The nutrient requirement amount calculating unit may further include an interaction processing unit for adjusting the nutrient requirement amount based on predetermined information about interaction of nutrients.

The nutrient requirement amount calculating unit may further include a restriction processing unit for adjusting the nutrient requirement amount based on predetermined restriction information about nutrient amount.

The apparatus for suggesting a blend of a nutritional supplement may further include a correlation processing unit for analyzing a correlation between a nutritional condition judged by the nutrient requirement amount calculating unit and a living environment acquired from an outer part, in regard to a plurality of people to be examined and a medical inquiry processing unit for designating the medical inquiry item to perform the medical inquiry on the person to be examined by using a result of the analysis of the correlation.

The apparatus for suggesting a blend of a nutritional supplement may further include a correlation processing unit for analyzing a correlation between a nutritional condition judged by the nutrient requirement amount calculating unit and a life goal predetermined by the person to be examined, in regard to a plurality of people to be examined and a medical inquiry processing unit for designating the medical inquiry item to perform the medical inquiry on the person to be examined by using a result of the analysis of the correlation.

The apparatus for suggesting a blend of a nutritional supplement may further include a preparation request receiving unit for receiving a preparation request of the nutritional supplement based on the blend suggested by the nutritional supplement suggesting unit from the person to be examined, wherein the preparation request receiving unit may allow the nutritional supplement suggesting unit to make a preparation request of the nutritional supplement to an outer part, in case of receiving the preparation request from the person to be examined.

The medical inquiry item may include an item to perform a medical inquiry about a taste, which is requested by the person to be examined, of the nutritional supplement suggested by the nutritional supplement suggesting unit, and the nutritional supplement suggesting unit may suggest a blend, to which an ingredient adjusting the nutritional supplement to have the taste designated by the person to be examined is added, as the blend of the nutritional supplement.

The medical inquiry item may include an item to perform a medical inquiry about a color, which is requested by the person to be examined, of the nutritional supplement suggested by the nutritional supplement suggesting unit, and the nutritional supplement suggesting unit may suggest a blend, to which an ingredient adjusting the nutritional supplement to have the color designated by the person to be examined is added, as the blend of the nutritional supplement.

The medical inquiry item may include an item to perform a medical inquiry about a smell, which is requested by the person to be examined, of the nutritional supplement suggested by the nutritional supplement suggesting unit, and the nutritional supplement suggesting unit may suggest a blend, to which an ingredient adjusting the nutritional supplement to have the smell designated by the person to be examined is added, as the blend of the nutritional supplement.

The medical inquiry item may include an item to perform a medical inquiry about a shape, which is requested by the person to be examined, of the nutritional supplement suggested by the nutritional supplement suggesting unit, and the nutritional supplement suggesting unit may suggest a blend based on the shape designated by the person to be examined.

According to the seventh aspect of the present invention, a blending apparatus of a nutritional supplement for blending nutrients to prepare the nutritional supplement based on a result of checking a nutritional condition of a person to be examined, includes a customer authentication inputting unit for acquiring customer identification information to identify the person to be examined from an outer part, a nutritional supplement blend acquiring unit for acquiring blend information about a blend of the nutritional supplement corresponding to the person to be examined from an outer part and a nutritional supplement blending unit for blending nutrients to prepare the nutritional supplement based on the blend information.

The customer authentication inputting unit may acquire the customer identification information from an outer part by using a recording medium on which the customer identification information is recorded.

The blending apparatus of a nutritional supplement as claimed may further include a preparation request receiving unit for receiving a preparation request of the nutritional supplement based on the blend information from the person to be examined, wherein the preparation request receiving unit may allow the nutritional supplement blending unit to blend nutrients to prepare the nutritional supplement, in case the person to be examined receives the preparation request.

The nutritional supplement blend acquiring unit may acquire information about a taste designated by the person to be examined from an outer part, and the nutritional supplement blending unit may add an ingredient, which adjusts a taste of the nutritional supplement based on the information about the taste designated by the person to be examined, to the nutritional supplement.

The nutritional supplement blend acquiring unit may acquire information about a color designated by the person to be examined from an outer part, and the nutritional supplement blending unit may add an ingredient, which adjusts a color of the nutritional supplement based on the information about the color designated by the person to be examined, to the nutritional supplement.

The nutritional supplement blend acquiring unit may acquire information about a smell designated by the person to be examined from an outer part, and the nutritional supplement blending unit may add an ingredient, which adjusts a smell of the nutritional supplement based on the information about the smell designated by the person to be examined, to the nutritional supplement.

The nutritional supplement blend acquiring unit may acquire information about a shape designated by the person to be examined from an outer part, and the nutritional supplement blending unit may select a shape of the nutritional supplement based on the information about the shape designated by the person to be examined.

According to the eighth aspect of the present invention, a blending apparatus of a nutritional supplement for blending nutrients to prepare the nutritional supplement based on a result of checking a nutritional condition of a person to be examined, includes a medical inquiry processing unit for presenting a medical inquiry item to the person to be examined and acquiring a response to a medical inquiry, a nutritional supplement blend acquiring unit for acquiring blend information indicating a blend of the nutritional supplement corresponding to the person to be examined by using the response to the medical inquiry and a nutritional supplement blending unit for blending nutrients to prepare the nutritional supplement based on the blend information.

The blending apparatus of a nutritional supplement may further include a customer authentication inputting unit for acquiring customer identification information to identify the person to be examined from an outer part, wherein the response to the medical inquiry, which corresponds to the person to be examined, may be renewed by using the customer identification information and the response to the medical inquiry.

The blending apparatus of a nutritional supplement may further include a preparation request receiving unit for receiving a preparation request of the nutritional supplement based on the blend information from the person to be examined, wherein the preparation request receiving unit may allow the nutritional supplement blending unit to blend nutrients to prepare the nutritional supplement, in case the person to be examined receives the preparation request.

The nutritional supplement blend acquiring unit may acquire information about a taste designated by the person to be examined from an outer part, and the nutritional supplement blending unit may add an ingredient, which adjusts a taste of the nutritional supplement based on the information about the taste designated by the person to be examined, to the nutritional supplement.

The nutritional supplement blend acquiring unit may acquire information about a color designated by the person to be examined from an outer part, and the nutritional supplement blending unit may add an ingredient, which adjusts a color of the nutritional supplement based on the information about the color designated by the person to be examined, to the nutritional supplement.

The nutritional supplement blend acquiring unit may acquire information about a smell designated by the person to be examined from an outer part, and the nutritional supplement blending unit may add an ingredient, which adjusts a smell of the nutritional supplement based on the information about the smell designated by the person to be examined, to the nutritional supplement.

The nutritional supplement blend acquiring unit may acquire information about a shape designated by the person to be examined from an outer part, and the nutritional supplement blending unit may select a shape of the nutritional supplement based on the information about the shape designated by the person to be examined.

According to the ninth aspect of the present invention, a blending system of a nutritional supplement for blending nutrients to prepare the nutritional supplement based on a result of checking a nutritional condition of a person to be examined from a response to a medical inquiry, includes an apparatus for suggesting a blend of the nutritional supplement for checking the nutritional condition of the person to be examined from the response to the medical inquiry and a blending apparatus of the nutritional supplement for blending nutrients to prepare the nutritional supplement suggested by the apparatus for suggesting a nutritional supplement, wherein the apparatus for suggesting a nutritional supplement may include a nutrient requirement amount calculating unit for calculating nutrient requirement amount of the person to be examined by acquiring the response to the medical inquiry corresponding to a medical inquiry item and a nutritional supplement suggesting unit for suggesting the blend of the nutritional supplement based on information about the nutrient requirement amount of the person to be examined acquired by the nutrient requirement amount calculating unit.

According to the tenth aspect of the present invention, a blending apparatus of a nutritional supplement for blending nutrients to prepare the nutritional supplement based on a result of checking a nutritional condition of a person to be examined, includes a medical inquiry processing unit for presenting a medical inquiry item to the person to be examined and acquiring a response to a medical inquiry, a nutrient requirement amount calculating unit for calculating nutrient requirement amount of the person to be examined from the response to the medical inquiry, a nutritional supplement suggesting unit for suggesting a blend of the nutritional supplement based on the nutrient requirement amount of the person to be examined and a nutritional supplement blending unit for blending nutrients to prepare the nutritional supplement based on the blend of the nutritional supplement.

The blending apparatus of a nutritional supplement may further include a preparation request receiving unit for receiving a preparation request of the nutritional supplement based on blend information from the person to be examined, wherein the preparation request receiving unit may allow the nutritional supplement blending unit to blend nutrients to prepare the nutritional supplement, in case the person to be examined receives the preparation request.

According to the eleventh aspect of the present invention, a blending apparatus of a nutritional supplement for blending nutrients to prepare a nutritional supplement based on a result of checking a nutritional condition of a person to be examined, includes a nutritional supplement blend acquiring unit for acquiring blend information indicating a blend of the nutritional supplement corresponding to the person to be examined from a portable recording medium on which the blend information is recorded and a nutritional supplement blending unit for blending nutrients to prepare the nutritional supplement based on the blend information.

BRIEF DESCRIPTION OF DRAWINGS

FIG. 4 shows an example of a personal information database 1200 according to an exemplary embodiment of the present invention.

FIG. 5 shows an example of a medical inquiry item database 1210 according to an exemplary embodiment of the present invention.

FIG. 6 shows an example of a medical inquiry history database 1230 according to an exemplary embodiment of the present invention.

FIG. 7 shows an example of a living environment database 1250 according to an exemplary embodiment of the present invention.

FIG. 8 shows an example of a medical inquiry response database 1220 according to an exemplary embodiment of the present invention.

FIG. 9 shows an example of a nutrient database 1240 according to an exemplary embodiment of the present invention.

FIG. 10 shows an example of a nutrient database 1260 according to an exemplary embodiment of the present invention.

FIG. 11 shows an example of a presumed disease name database 1280 according to an exemplary embodiment of the present invention.

FIG. 12 shows an example of a medical institution database 1290 according to an exemplary embodiment of the present invention.

FIG. 13 shows an example of a correlation database 1270 according to an exemplary embodiment of the present invention.

DETAILED DESCRIPTION OF THE INVENTION

The invention will now be described based on the preferred embodiments, which do not intend to limit the scope of the present invention, but exemplify the invention. All of the features and the blends thereof described in the embodiment are not necessarily essential to the invention.

Figure 1:
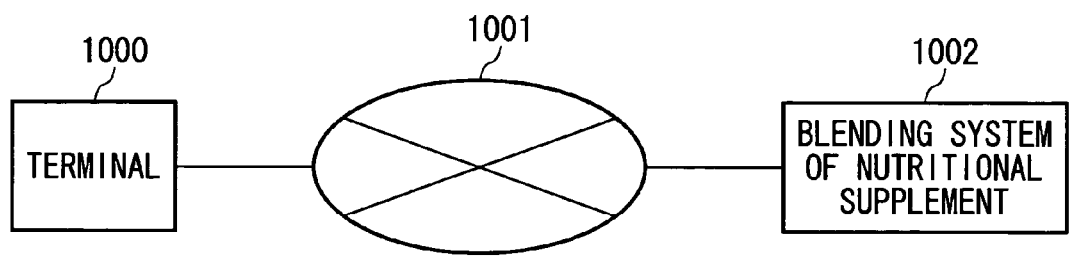
FIG. 1 shows a client-server type calculator system including a blending system of a nutritional supplement according to an exemplary embodiment of the present invention.

FIG. 1 shows a client-server type calculator system including a blending system of a nutritional supplement according to an exemplary embodiment of the present invention. The calculator system includes a terminal 1000, a network 1001 and a blending system of a nutritional supplement 1002.

The terminal 1000 is for a customer, a person to be examined, to access the blending system of a nutritional supplement 1002. The network 1001 allows the terminal 1000 and the blending system of a nutritional supplement 1002 to be coupled each other. The network 1001 may be the Internet, the local area network, the public switched telephone network or any blend of those.

The blending system of a nutritional supplement 1002 provides a customer, who accesses it via the network 1001 through the terminal 1000, with a service to prepare nutritional supplements desired by the customer. The nutritional supplements prepared by the blending system of a nutritional supplement 1002 arrive at the customer through means such as a delivery, receipt at the store or the like.

Figure 2:
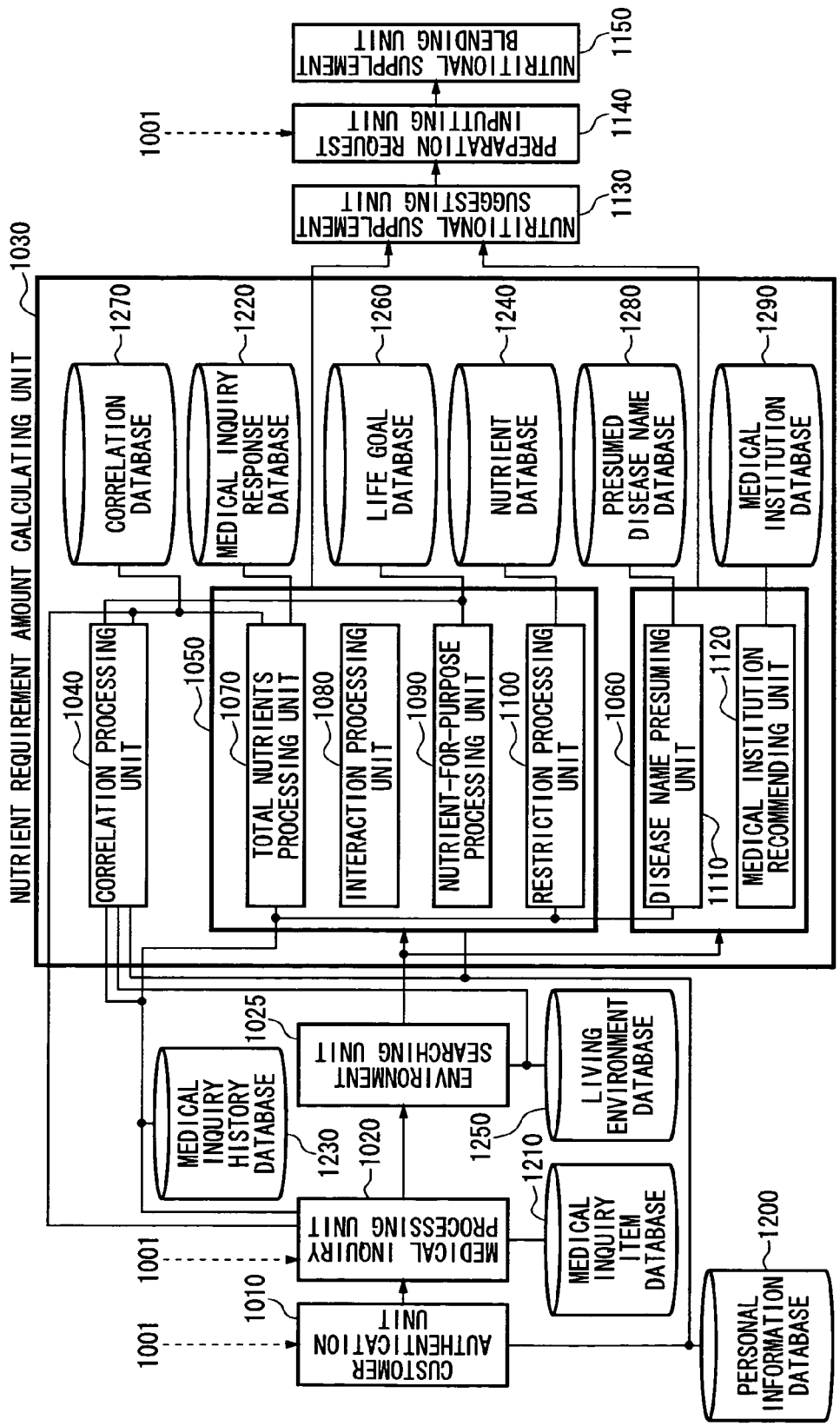
FIG. 2 shows an example of a blending system of a nutritional supplement 1002 according to an exemplary embodiment of the present invention.

FIG. 2 shows an example of the configuration of a blending system of a nutritional supplement 1002 according to an exemplary embodiment of the present invention.

The blending system of a nutritional supplement 1002 includes a customer authenticating unit 1010, a medical inquiry processing unit 1020, an environment searching unit 1025, a nutrient requirement amount calculating unit 1030, a nutritional supplement suggesting unit 1130, a preparation request inputting unit 1140, a nutritional supplement blending unit 1150, a personal information database 1200, a medical inquiry item database 1210, a medical inquiry history database 1230, and a living environment database 1250.

The medical inquiry processing unit 1020 is an example of a medical inquiry response acquiring unit and a medical inquiry processing unit according to the present invention. The environment searching unit 1025 is an example of a living environment searching unit and a workplace living environment searching unit according to the present invention. The nutrient requirement amount calculating unit 1030 is an example of an insufficient nutrient processing unit and a nutrient requirement amount calculating unit according to the present invention. The preparation request inputting unit 1140 is an example of a preparation request receiving unit according to the present invention.

The customer authenticating unit 1010 performs authentication on a customer who accesses it via the network 1001 with the terminal 1000 by using customer ID in the personal information database 1200. And, the customer authenticating unit 1010 acquires the personal information of the customer in the personal information database 1200 and sends it to the medical inquiry processing unit 1020.

The medical inquiry processing unit 1020 selects medical inquiry items for the customer based on the medical inquiry item data in the medical inquiry item database 1210, the medical inquiry history in the medical inquiry history database 1230 and the correlation between the living environment or the life goal and the insufficient degree of nutrient in the correlation database 1270, and sends them to the terminal 1000 via the network 1001. In addition, the medical inquiry processing unit 1020 acquires the response to the medical inquiry from the terminal 1000 via the network and sends the personal information received from the customer authenticating unit 1010 and the response to the medical inquiry to the environment searching unit 1025.

The environment searching unit 1025 searches the living environment of the region from the living environment database 1250 by using the address and the address of the workplace included in the personal information of the customer received from the medical inquiry processing unit 1020 and adds it to the response to the medical inquiry.

And, the environment searching unit 1025 sends the personal information of the customer received from the medical inquiry processing unit 1020 and the added response to the medical inquiry to the nutrient requirement amount calculating unit 1030.

The nutrient requirement amount calculating unit 1030 calculates the nutrient requirement amount indicating the amount of nutrient the customer has to take in a day based on the personal information of the customer and the response to the medical inquiry received from the environment searching unit 1025 and the medical inquiry history in the medical inquiry history database 1230. And, it sends the calculated nutrient requirement amount and the personal information of the customer received from the environment searching unit 1025 to the nutritional supplement suggesting unit 1130. In addition, if the customer is presumed to be sick as the result of the medical inquiry, the nutrient requirement amount calculating unit 1030 sends the medical treatment recommendation information including the presumed disease name and the recommended medical institution to the nutritional supplement suggesting unit 1130.

The nutritional supplement suggesting unit 1130 generates the blend information about the nutritional supplement based on the nutrient requirement amount received from the nutrient requirement amount calculating unit 1030. The blend of nutritional supplements result from a blend of ready-made nutritional supplements and nutritional supplements newly determined for the customer. And, the nutritional supplement suggesting unit 1130 sends the generated blend information to the preparation request inputting unit 1140 together with the personal information of the customer received from the nutrient requirement amount calculating unit 1030. In addition, if the nutritional supplement suggesting unit 1130 receives the medical treatment recommendation information from the nutrient requirement amount calculating unit 1030, it sends the medical treatment recommendation information to the preparation request inputting unit 1140.

The preparation request inputting unit 1140 checks whether the customer requests the preparation of the nutritional supplement based on the blend information received from the nutritional supplement suggesting unit 1130. In other words, the preparation request inputting unit 1140 allows the terminal 1000 to display the blend information and a message, e.g., "Do you request us to prepare the nutritional supplement based on this blend?", via the network 1001 for the customer. And, the preparation request inputting unit 1140 allows the customer to input whether to request the preparation and the amount of the nutritional supplement to be prepared in case of requesting the preparation by using the terminal 1000. And, when the customer requests the preparation, the preparation request inputting unit 1140 sends the blend information to the nutritional supplement blending unit 1150 together with the personal information of the customer received from the nutritional supplement suggesting unit 1130. And, if the preparation request inputting unit 1140 receives the medical treatment recommendation information from the nutritional supplement suggesting unit 1130, it informs the customer of the medical treatment recommendation information. That is, the preparation request inputting unit 1140 sends the medical treatment recommendation information to the terminal 1000 via the network 1001 to display the medical treatment recommendation information.

In addition, the preparation request inputting unit 1140 may send the blend information received from the nutritional supplement suggesting unit 1130 to the terminal 1000 of the customer via the network 1001. Therefore, the terminal 1000 can record the blend information onto a recording medium such as a hard disk drive, a magnetic card, an IC card, flash memory or the like.

The nutritional supplement blending unit 1150 blends nutrients for a nutritional supplement based on the blend information received from the preparation request inputting unit 1140. And, it outputs the blended nutritional supplement to an addressee based on the personal information of the customer received from the preparation request inputting unit 1140. The output to the addressee may be a means such as a destination label for delivery or an identification label.

The nutrient requirement amount calculating unit 1030 has a nutrient amount processing unit 1050, a medical treatment recommending unit 1060, a correlation processing unit 1040, a medical inquiry response database 1220, a nutrient database 1240, a life goal database 1260, a presumed disease name database 1280, a medical institution database 1290 and a correlation database 1270.

The nutrient amount processing unit 1050 calculates the nutrient requirement amount for the customer based on the personal information of the customer received from the environment searching unit 1025 and the response to the medical inquiry. And, it sends the calculated nutrient requirement amount to the nutritional supplement suggesting unit 1130 together with the personal information of the customer received from the environment searching unit 1025.

The nutrient amount processing unit 1050 includes a total nutrients processing unit 1070, an interaction processing unit 1080, a nutrient-for-purpose processing unit 1090 and a restriction processing unit 1100.

Before calculating the nutrient requirement amount for the customer, the total nutrients processing unit 1070 calculates the insufficient degree of nutrient by using the response to the medical inquiry received from the environment searching unit 1025 and the medical inquiry history in the medical inquiry history database 1230.

The medical inquiry response database 1220 holds a value to be added to the insufficient degree of nutrient corresponding to each response to the medical inquiry. The total nutrients processing unit 1070 searches the medical inquiry response database 1220 to acquire the insufficient degree to be added for each response to the medical inquiry when calculating the insufficient degree of nutrient. And, the total nutrients processing unit 1070 accumulates the insufficient nutrient corresponding to the response to the medical inquiry for each response to the medical inquiry in order to calculate the insufficient degree of nutrient.

In addition, the total nutrients processing unit 1070 refers to the medical inquiry history in the medical inquiry history database 1230 when calculating the insufficient degree of nutrient. That is, it calculates the insufficient degree of nutrient by adding the response to the medical inquiry based on the history of the response to the medical inquiry held in the medical inquiry history database 1230 in regard to the medical inquiry item the medical inquiry processing unit 1020 does not carry out to the customer at that time.

And, the total nutrients processing unit 1070 stores the insufficient degree of nutrient calculated in the above process into the medical inquiry history database 1230.

Next, the total nutrients processing unit 1070, the interaction processing unit 1080, the nutrient-for-purpose processing unit 1090, and the restriction processing unit 1100 calculates the nutrient requirement amount of the customer based on the insufficient degree of nutrient calculated by the total nutrients processing unit 1070.

The total nutrients processing unit 1070 sets an initial value of the nutrient requirement amount of the customer to be the insufficient degree of nutrient calculated by the total nutrients processing unit 1070. And, the total nutrients processing unit 1070 performs a process of adding the nutrient in an integrated manner, e.g. adding total nutrients corresponding to the number of insufficient nutrients for the nutrient requirement amount.

The interaction processing unit 1080 adjusts the nutrient requirement amount calculated by the total nutrients processing unit 1070 based on the interaction of nutrients. The interaction represents an action in which the ingestion amount of one nutrient affects the ingestion amount of another nutrient. In the interaction, there are two actions; synergistic effect and antagonism.

The synergistic effect represents a useful action in which ingesting one nutrient causes to help the absorption of another nutrient. For example, according to "A Method for Ingesting Vitamin Mineral Recommended by A Pharmacist (2nd Edition)" (Tohru HUkUI, Maruzen Co., Ltd., p. 68), Vitamin D helps to absorb Ca, Phosphorus and Vitamin A.

The antagonism represents an action in which ingesting one nutrient excessively causes another the nutrient to be insufficient. For example, according to "A Way of Ingesting Vitamin and Mineral Recommended by A Pharmacist (2nd Edition)" (Tohru HUkUI, Maruzen Co., Ltd., p. 121), Phosphorus is closely related to calcium, and the lack or surplus of them affects each other.

The interaction processing unit 1080 adjusts the nutrient requirement amount considering the balance of the nutrients having the interaction based the interaction represented above.

The nutrient-for-purpose processing unit 1090 adjusts the nutrient requirement amount adjusted by the interaction processing unit 1080 based on a life goal designated by the customer. The life goal represents a goal on nutrition which a customer desires to realize by using the blending system of a nutritional supplement 1002. The life goal database 1260 holds the amount of nutrient to be added for each life goal. The nutrient-for-purpose processing unit 1090 searches the life goal database 1260 and acquires the nutrient and the amount to be added corresponding to the life goal during adjusting the nutrient requirement amount.

The restriction processing unit 1100 adjusts the nutrient requirement amount adjusted by the nutrient-for-purpose processing unit 1090 based on restriction information such as a predetermined amount to be needed or an upper limit ingestion amount per a day for each nutrient. In the present embodiment, the predetermined amount to be needed and the upper limit ingestion amount per a day are determined based on the data from Health, Labor and Welfare Ministry (cf. "Visual Wide Food Composition Table in accordance to 'Japanese Food Standard Composition Table'", Resource Council, Japan Science and Technology Agency, Tokyo Shoseki, p.

280 to 283). The nutrient database 1240 holds the amount to be needed and the upper limit ingestion amount of the nutrient for each nutrient. The restriction processing unit 1100 searches the nutrient database 1240 and acquires the amount to be needed and the upper limit ingestion amount corresponding to each nutrient when adjusting the nutrient requirement amount.

By the sequence described above, the nutrient amount processing unit 1050 calculates the nutrient requirement amount of the customer by using the total nutrients processing unit 1070, the interaction processing unit 1080, the nutrient-for-purpose processing unit 1090 and the restriction processing unit 1100.

When the nutritional supplement blending unit 1150 prepares the nutritional supplement based on the nutrient requirement amount, the restriction processing unit 1100 stores the nutrient requirement amount of the nutritional supplement prepared into the medical inquiry history database 1230.

The medical treatment recommending unit 1060 sends the medical treatment recommendation information to the nutritional supplement suggesting unit 1130 if the customer is presumed to be sick as the result of the medical inquiry. The medical treatment recommending unit 1060 includes a disease name presuming unit 1110 for presuming the name of the disease and a medical institution recommending unit 1120 for recommending a medical institution.

The disease name presuming unit 1110 presumes the name of the disease based on the information held by the presumed disease name database 1280. The presumed disease name database 1280 holds a presumption condition representing a condition of the response to the medical inquiry and the nutritional condition, the presumed disease name representing the name of the disease presumed in case the presumption condition is satisfied and a medical department capable of performing treatment of the disease presumed.

The medical institution recommending unit 1120 recommends a medical institution based on the information held by the medical institution database 1290. The medical institution database 1290 holds the name of the medical institution, the medical department, the address and the contact place. The medical institution recommending unit 1120 searches the medical institution database 1290 taking the address of the customer included in the personal information of the customer and the medical department outputted by the disease name presuming unit 1110 as a key, and acquires the medical institution having the medical department at a place adjacent to the customer.

The correlation processing unit 1040 analyzes the correlation between the living environment or the life goal and the insufficient degree of nutrient, and stores it into the correlation database 1270. In the present embodiment, the living environment, which is the object of the correlation processing unit 1040, includes the eating habit such as the content of meal of the customer held by the medical inquiry history database 1230 as the response to the medical inquiry, the health life such as the stress level of the customer, drinking, smoking, the amount of exercise or the like held by the medical inquiry history database 1230 as the response to the medical inquiry and the address and the address of the workplace of the personal information database 1200 or the residential environment held by the medical inquiry history database 1230 as response to the medical inquiry.

Figure 3:
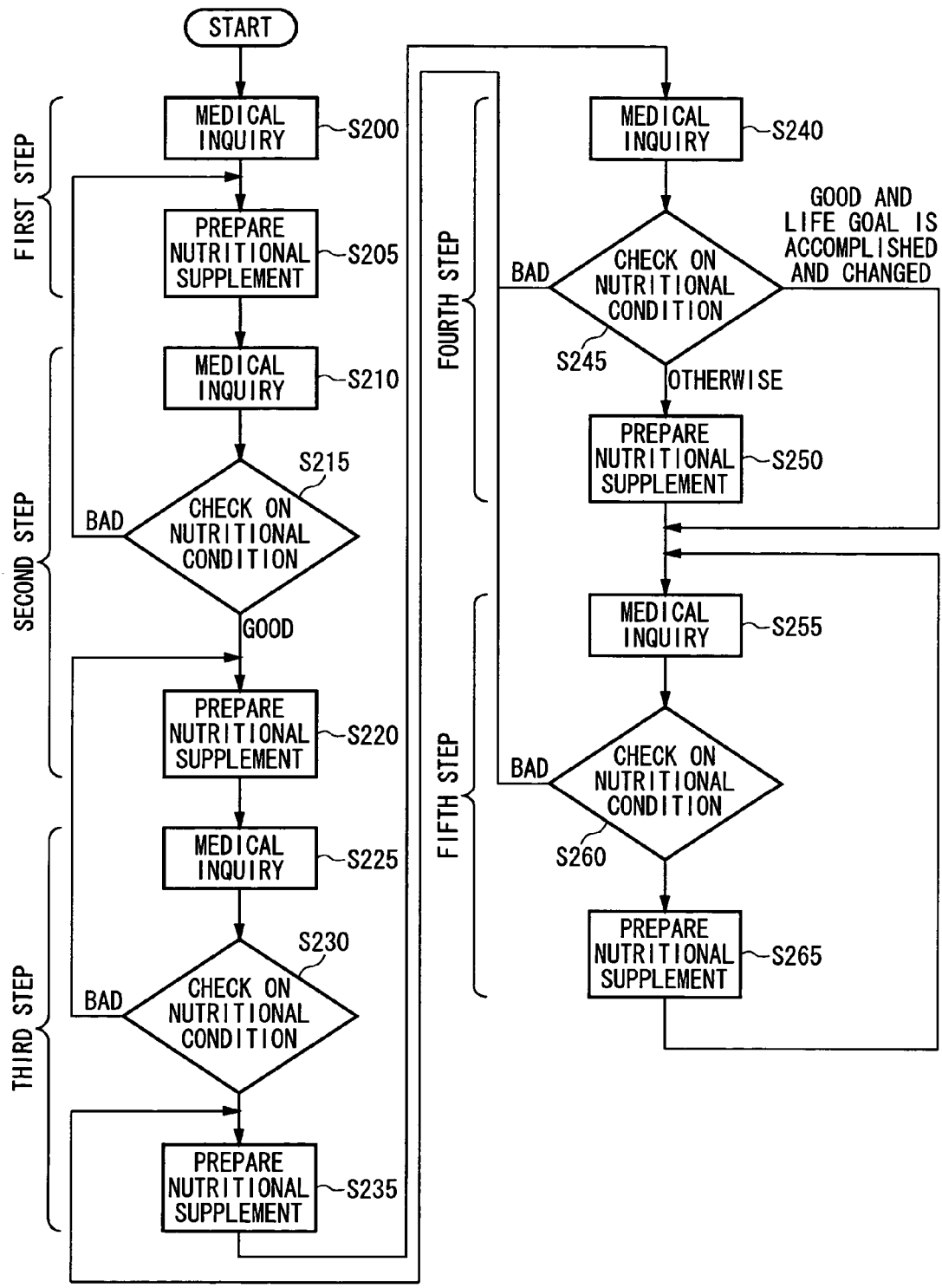
FIG. 3 is a flowchart that shows a preparation flow of a nutritional supplement according to an exemplary embodiment of the present invention.

FIG. 3 is a flowchart that shows a flow of preparing a nutritional supplement by using the blending system of a nutritional supplement 1002 according to an exemplary embodiment of the present invention.

According to the present embodiment, the blending system of a nutritional supplement 1002 helps to improve the nutritional condition of the customer by using the five steps.

First, the customer authenticating unit 1010 assigns the customer ID when adding a new customer, and registers the personal information of the customer into the personal information database 1200. Then, the medical inquiry processing unit 1020 performs the medical inquiry of the first step to the new customer via the network 1001 and the terminal 1000 (S200).

Next, the nutritional supplement of the first step is prepared based on the inquiry result of the first step (S205). In manufacturing the nutritional supplement, the nutrient amount processing unit 1050 calculates the nutrient requirement amount based on the result of the medical inquiry to the customer, the nutritional supplement suggesting unit 1130 suggests a blend of the nutritional supplement based on the nutrient requirement amount, the preparation request inputting unit 1140 receives the preparation request of the nutritional supplement based on the blend from the customer and the nutritional supplement blending unit 1150 blends nutrients for the nutritional supplement corresponding to the customer.

It is the object of the first step to perform the blend of the nutritional supplement to add nutrients in an integrated manner. Accordingly, the nutrient-for-purpose processing unit 1090 does not adjust the nutrient requirement amount corresponding to the life goal of the customer. In other words, the nutrient amount processing unit 1050 calculates the nutrient requirement amount by using the total nutrients processing unit 1070, the interaction processing unit 1080 and the restriction processing unit 1100. Therefore, the nutritional supplement suggesting unit 1130 can suggest a blend of the nutritional supplement supplying nutrients in an integrated manner by using the nutrient requirement amount calculated by the total nutrients processing unit 1070, the interaction processing unit 1080 and the restriction processing unit 1100.

Next, the medical inquiry processing unit 1020 performs the medical inquiry of the second step to the customer via the network 1001 and the terminal 1000 (S210).

Then, the nutrient amount processing unit 1050 checks on the nutritional condition of the customer (S215). In the present checking process, the nutrient amount processing unit 1050 judges the nutritional condition of the customer based on the insufficient degree of nutrient calculated by the total nutrients processing unit 1070 using the result of the medical inquiry. The nutritional condition is judged to be bad, for example, in case the number of the nutrients of which the insufficient degree is more than 100% is equal to or more than 50% among nutrients managed by the blending system of a nutritional supplement 1002. In addition, the judgment condition for the nutritional condition may include a condition whether the response to the medical inquiry of "have you taken in the previous nutritional supplement?" is "No" or not.

The nutrient amount processing unit 1050 continues to prepare the nutritional supplement of the first step in case the judgment result is bad (S205).

Next, the nutritional supplement of the second step is prepared based on the result of the medical inquiry of the second step (S220).

It is the object of the second step to perform the blend of the nutritional supplement to mainly add insufficient nutrients. Therefore, the nutrient-for-purpose processing unit 1090, like the first step, does not adjust the nutrient requirement amount corresponding to the life goal of the customer. In addition, the amount of the total nutrients to be added to the nutrient requirement amount in an integrated manner by the total nutrients processing unit 1070 and the amount of the nutrient requirement adjusted by the interaction processing unit 1080 are decreased in comparison to the first step. Further, the restriction processing unit 1100 reduces the upper limit of the nutrient requirement amount corresponding to the nutrients which are not insufficient in comparison to the first step.

Next, the medical inquiry processing unit 1020 performs the medical inquiry of the third step to the customer via the network 1001 and the terminal 1000 (S225).

Then, the nutrient amount processing unit 1050 checks on the nutritional condition of the customer (S230). In the present checking process, the nutrient amount processing unit 1050 judges the nutritional condition of the customer, like the second step, based on the insufficient degree of nutrient calculated by the total nutrients processing unit 1070 using the result of the medical inquiry. The nutrient amount processing unit 1050 continues to prepare the nutritional supplement of the second step in case the judgment result is bad (S220).

Next, the nutritional supplement of the third step is prepared based on the result of the medical inquiry of the third step (S235).

It is the object of the third step to perform the blend of the nutritional supplement to mainly add nutrients corresponding to the life goal of the customer for whom the nutrients are satisfied in an integrated manner through the first step and the second step.

Therefore, the nutrient-for-purpose processing unit 1090 adjusts the nutrient requirement amount corresponding to the life goal of the customer. In addition, the amount of the total nutrients to be added to the nutrient requirement amount in an integrated manner by the total nutrients processing unit 1070 and the amount of the nutrient requirement adjusted by the interaction processing unit 1080 are decreased in comparison to the second step. Further, the restriction processing unit 1100 reduces the upper limit of the nutrient requirement amount corresponding to the nutrients which are not insufficient in comparison to the second step.

Next, the medical inquiry processing unit 1020 performs the medical inquiry of the fourth step to the customer via the network 1001 and the terminal 1000 (S240). In the fourth step, the medical inquiry processing unit 1020 generates the medical inquiry items capable of pursuing the reason of the nutrients liable to be insufficient for the customer based on the data accumulated by the medical inquiry history database 1230 until that time.

Then, the nutrient amount processing unit 1050 checks on the nutritional condition of the customer (S245). In the present checking process, the nutrient amount processing unit 1050 judges the nutritional condition of the customer, like the second step, based on the insufficient degree of nutrient calculated by the total nutrients processing unit 1070 using the result of the medical inquiry.

The nutrient amount processing unit 1050 continues to prepare the nutritional supplement of the third step in case the judgment result is bad (S235). In addition, the nutrient amount processing unit 1050 continues to prepare the nutritional supplement of the fifth step in case the judgment result is good, the life goal is accomplished and the life goal is changed (S255).

Next, the nutritional supplement of the fourth step is prepared based on the result of the medical inquiry of the fourth step (S250).

It is the object of the fourth step to perform the blend of the nutritional supplement to mainly add nutrients necessary to achieve the life goal and liable to be insufficient for the customer.

Therefore, the nutrient-for-purpose processing unit 1090 adjusts the nutrient requirement amount corresponding to the life goal of the customer. In addition, the process of adding the total nutrients to the nutrient requirement amount in an integrated manner by the total nutrients processing unit 1070 and the process of adjusting the nutrient requirement amount by the interaction processing unit 1080 are not performed.

Next, the medical inquiry processing unit 1020 performs the medical inquiry of the fifth step to the customer via the network 1001 and the terminal 1000 (S255). In the fifth step, the medical inquiry processing unit 1020 generates the medical inquiry items at an interval determined for each medical inquiry item.

Then, the nutrient amount processing unit 1050 checks on the nutritional condition of the customer (S260). In the present checking process, the nutrient amount processing unit 1050 judges the nutritional condition of the customer, like the second step, based on the insufficient degree of nutrient calculated by the total nutrients processing unit 1070 using the result of the medical inquiry.

The nutrient amount processing unit 1050 continues to prepare the nutritional supplement of the third step in case the judgment result is bad (S235).

Next, the nutritional supplement of the fifth step is prepared based on the result of the medical inquiry of the fifth step (S265).

It is the object of the fifth step to perform the blend of the nutritional supplement to mainly add nutrients necessary to achieve the life goal and liable to be insufficient for the customer like the fourth step and to perform the medical inquiry for judging the nutritional condition of the customer at the interval determined for each medical inquiry item.

Therefore, the nutrient-for-purpose processing unit 1090 adjusts the nutrient requirement amount corresponding to the life goal of the customer. In addition, the process of adding the total nutrients to the nutrient requirement amount in an integrated manner by the total nutrients processing unit 1070 and the process of adjusting the nutrient requirement amount by the interaction processing unit 1080 are not performed.

When the preparation of the nutritional supplement of the fifth step (S265) has been finished, the nutrient amount processing unit 1050 continues to perform the medical inquiry of the fifth step (S255).

The personal information database 1200 holds a value indicating the step needed to realize the processes described above for each customer. In addition, the nutrient amount processing unit 1050 renews a value indicating the step at which the customer is in the personal information database 1200 every time the step on processing, at which the customer is, is changed.

Accordingly, the blending system of a nutritional supplement 1002 can provide the flow of preparing the nutritional supplement through the access of the customer a plurality of times, wherein, for example, it prepares the nutritional supplement for two weeks by performing the medical inquiry of the first step when the customer accesses it for the first time (S200 and S205) and it prepares the nutritional supplement for two weeks by performing the medical inquiry of the second step when the customer accesses it next time (S210, S215 and S220).

By the processes above, it is possible to realize the blending system of a nutritional supplement 1002 for first suggesting the nutritional supplement to add nutrients for the customer in an integrated manner and then gradually suggesting the nutritional supplement to add nutrients necessary to achieve the life goal and liable to be insufficient for the customer.

FIG. 4 shows an example of a personal information database 1200 according to an exemplary embodiment of the present invention. The personal information database 1200 according to the present embodiment holds the customer ID, the name, the date of birth, the sex, the address, the address of the workplace, the life goal, the preference for the nutritional supplement and the step, at which the customer is at the present time, for each customer. The personal information database 1200 may alternatively hold the personal information such as the authentication password, the contact place of the customer, e.g. the telephone number, the mail address or the like, the settlement method, e.g. the account number or the credit card number.

In the present embodiment, the life goal held in the personal information database 1200 is identified by using a life goal ID of which the value is one of "0" then there is no life goal, "1" then it means the improvement of the immunity, "2" then the countermeasure against dry skin and "3" then the countermeasure against skin problems. The personal information database 1200 may alternatively assign a plurality of the life goal simultaneously by using for example a bitmap.

The life goal held in the personal information database 1200 according to the present embodiment holds the color, taste, smell and package method of the nutritional supplement as the preference of the nutritional supplement.

The color of the nutritional supplement is identified by using a nutritional supplement color ID of which the value is one of "0" then there is no color, "1" then it means yellow and "2" then red. The nutritional supplement suggesting unit 1130 adds pigments to the blend of the nutritional supplement based on the designated color. In other words, if the color of the nutritional supplement is designated as "1" of yellow, a pigment such as a cartenoid or gardenia is added to the blend of the nutritional supplement. In addition, if the color of the nutritional supplement is designated as "2" of red, a pigment such as a red cabbage, monascus, lycopene or the like to the blend of the nutritional supplement. The various colors of the nutritional supplement can be realized by using other pigments.

The taste of the nutritional supplement is identified by using a nutritional supplement taste ID of which the value is one of "0" then there is no adjustment, "1" then it means a sweetener consisting of non-calorie sugar, "2" then a sweetener of a pleasant aftertaste using aspartame and "3" then a sweetener added with the functions of the intestines using oligosaccharide. The nutritional supplement suggesting unit 1130 adds condiments to the blend of the nutritional supplement based on the taste designated. The various tastes of the nutritional supplement can be realized by using other condiments.

The smell of the nutritional supplement is identified by using a nutritional supplement smell ID of which the value is one of "0" then there is no adjustment and "1" then it means a vanilla flavor. The nutritional supplement suggesting unit 1130 adds smell to the blend of the nutritional supplement based on the smell designated. The various smells of the nutritional supplement can be realized by using other flavorings.

The package method of the nutritional supplement, which is to designate the shape such as a form or size of the nutritional supplement, is identified by using a nutritional supplement package ID of which the value is one of "0" then there is no adjustment, "1" then it means a liquid form, "2" then a tablet form, "3" then soft capsules, "4" then a separation into small capsules and "5" then a granules form. The nutritional supplement suggesting unit 1130 selects a package method of the nutritional supplement based on the package method designated. The various package methods of the nutritional supplement can be realized by using other methods.

As described above, by designating the color, taste, smell and package method of the nutritional supplement, the blending system of a nutritional supplement 1002 can suggest the nutritional supplement suitable for the preference of the customer.

FIG. 5 shows an example of a medical inquiry item database 1210 according to an exemplary embodiment of the present invention. The medical inquiry item database 1210 according to the present embodiment hold the medical inquiry ID, the medical inquiry message, the branching destination for a response, the medical inquiry designation for a step, the medical inquiry designation for a life goal, the medical inquiry interval and the medical inquiry designation for an insufficient nutrient, for each medical inquiry item.

The medical inquiry ID is an identifier identifying the medical inquiry item. The medical inquiry message indicates the content of the medical inquiry made to the customer as the medical inquiry item. The medical inquiry processing unit 1020 according to the present invention requests the response of a numerical value for a medical inquiry item listed as "[numerical value]" in the medical inquiry message, and otherwise requests the customer to select one of third responds of "Yes" ("Y" in the drawing), "rather Yes" ("NY" in the drawing) or "No" (in the drawing "N").

In the branching destination for a response, the medical inquiry ID of the medical inquiry item to be performed next is designated for each response to the medical inquiry.

The response to the medical inquiry is one of third responds of "Y", "NY" or "N" except the medical inquiry IDs 1003 and 1004 listed as "[numerical value]" in the medical inquiry message. In the branching destination for a response, the medical inquiry ID of the medical inquiry item to be performed next is designated corresponding to the response to the medical inquiry.

Here, if the branching destination for a response is "0", the medical inquiry item of the next line is selected. In addition, if the branching destination for a response is "9999", the completion of the medical inquiry is selected.

In the medical inquiry designation for a step, whether to perform the medical inquiry of the medical inquiry item corresponding to the step of the customer is designated. For example, the medical inquiry ID 1000 is designated to perform the medical inquiry through the first step, the second step, the third step and the fifth step.

In the medical inquiry designation for a life goal, whether to perform the medical inquiry of the medical inquiry item corresponding to the life goal of the customer or not is designated. For example, the medical inquiry ID 1000 is designated to perform the medical inquiry in regard to all of the life goals of "1", "2" and "3".

In the medical inquiry interval, the interval to perform the medical inquiry of the medical inquiry item is designated. For example, the medical inquiry ID 1000 is designated to perform the medical inquiry every week. In addition, the medical inquiry ID 2000 is designated to perform the medical inquiry every time of performing the medical inquiry process.

In the medical inquiry for an insufficient nutrient, performing the medical inquiry item is designated in case the insufficient degree of nutrient by the previous result of the medical inquiry indicates the designated nutrient to be insufficient. In the present embodiment, the nutrient ID, which is an identifier having a value of 1 to 21, is given to the nutrient. In the present embodiment, the nutrient ID is assigned to be "1" for Vitamin A, "2" for Vitamin D, "3" for Vitamin E, "4" for Vitamin K, "5" for Vitamin B1, "6" for Vitamin B2, "7" for niacin, "8" for pantothenic acid, "9" for Vitamin B6, "10" for Vitamin B12, "11" for folic acid, "12" for biotin, "13" for Vitamin C, "14" for Vitamin P, "15" for iron, "16" for zinc, "17" for selenium, "18" for chrome, "19" for iodine, "20" for calcium and "21" for magnesium. If the medical inquiry designation for an insufficient nutrient is not checked for all nutrients, the medical inquiry item indicates an item to perform the medical inquiry not related with the insufficient degree of nutrient.

FIG. 6 shows an example of a medical inquiry history database 1230 according to an exemplary embodiment of the present invention. The medical inquiry history database 1230 according to the present embodiment holds the customer ID, the registration date, the kink of history, the medical inquiry ID or the nutrient ID and the response to the medical inquiry, the insufficient degree or the nutrient requirement amount. The data stored in the medical inquiry history database 1230 is the information indicating the response to the medical inquiry, the insufficient degree of nutrient based on the response to the medical inquiry and the blend of the nutritional supplement prepared according to the preparation request of the customer.

The response to the medical inquiry is the line in which the kind of history is designated as "medical inquiry". Each line consists of the customer ID, the registration date, the medical inquiry ID and the response to the medical inquiry of the medical inquiry item of the medical inquiry ID. For example, the first line of the table shown in FIG. 6 indicates that the customer designated as the customer ID 001 responded as "Y", namely, "Yes" to the medical inquiry item of the medical inquiry ID 1000 on Jan. 1, 1999.

The insufficient degree of nutrient is the line in which the kind of history is designated as "insufficient degree of nutrient". Each line consists of the customer ID, the registration date, the nutrient ID and the insufficient degree of nutrient of the nutrient ID. For example, the line, in which the kind of history is "insufficient degree of nutrient", of the table shown in FIG. 6 indicates that the insufficient degree of the nutrient (Vitamin A) of the nutrient ID1 in regard to the customer designated as the customer ID 001 is 2400 IU, 133% of the required amount per day, on Jan. 1, 1999.

The information indicating the blend of the nutritional supplement is the line in which the kind of history is designated as "preparation". Each line consists of the customer ID, the registration date, the nutrient ID and the nutrient requirement amount. For example, the line, in which the kind of history is "preparation", of the table shown in FIG. 6 indicates that the nutrient requirement amount of the nutrient (Vitamin A) of the nutrient ID1 in regard to the customer designated as the customer ID 001 is 1800 IU on Jan. 1, 1999 and the nutritional supplement is prepared based on this data.

FIG. 7 shows an example of a living environment database 1250 according to an exemplary embodiment of the present invention. The living environment database 1250 according to the present embodiment holds the address, the medical inquiry ID, and the response to the medical inquiry.

When the environment searching unit 1025 sends the response to the medical inquiry received from the medical inquiry processing unit 1020 to the nutrient requirement amount calculating unit 1030, it searches the living environment database 1250 by using the address and the address of the workplace included in the personal information of the customer and adds the response to the medical inquiry. For example, in case of the customer of the customer ID 001 registered in the personal information database 1200 in FIG. 4, the address is Saitama-ken and the address of the workplace is Shinjuku-ku Tokyo. The environment searching unit 1025 searches the living environment database 1250 based on the address and the address of the workplace and obtains the responses of "NY" for the address and "Y" for the address of the workplace to the medical inquiry of the medical inquiry ID 1000, i.e., "Are you affected by air pollution?" in the medical inquiry item database shown in FIG. 5. The environment searching unit 1025 selects "Y" of the response to the medical inquiry, which causes the nutrient to be insufficient, from the responses to the medical inquiry, and changes the response to the medical inquiry of into the medical inquiry ID 1000 into "Y".

By the processes above, the environment searching unit 1025 can add the response to the medical inquiry based on the living environment information of the living environment database 1250 by using the address and the address of the workplace.

The environment searching unit 1025 may alternatively set the average of the response to the medical inquiry of the address and the response to the medical inquiry of the address of the workplace to be the response to the medical inquiry. In addition, the living environment database 1250 may have the numerical value indicating the pollution degree of atmosphere of each address, and the environment searching unit 1025 may obtain the response to the medical inquiry by calculating the numerical value.

FIG. 8 shows an example of a medical inquiry response database 1220 according to an exemplary embodiment of the present invention. The medical inquiry response database 1220 according to the present embodiment holds the medical inquiry ID and the insufficient degree of each nutrient corresponding to the medical inquiry ID.

In the present embodiment, the insufficient degree of nutrient holds the insufficient degree in case the response to the medical inquiry is "Yes" to be separated corresponding to the required amount per a day determined for each nutrient. In addition, in the present embodiment, the insufficient degree in case the response to the medical inquiry is "rather Yes" is half the case that the response to the medical inquiry is "Yes".

For example, the first line of FIG. 8 holds the insufficient degree of nutrient for "Are you affected by air pollution?" of the medical inquiry ID 1000. The total nutrients processing unit 1070 increases the insufficient degree of Vitamin A by 30% of the required amount per a day, in case the customer responses "Yes" to the medical inquiry item. In addition, the total nutrients processing unit increases the insufficient degree of Vitamin A by 15% of the required amount per a day, in case the customer responses "rather Yes" to the medical inquiry item.

FIG. 9 shows an example of a nutrient database 1240 according to an exemplary embodiment of the present invention. The nutrient database 1240 according to the present embodiment holds the sex, the age, the nutrient ID, the required amount and the upper limit ingestion amount.

For example, the first line of FIG. 9 indicates that the required amount of the nutrient ID1, i.e. Vitamin A per a day is 1800 IU (IU: International Unit) and the upper limit ingestion amount per a day is 5000 IU for a woman of age 18 to 29.

FIG. 10 shows an example of a nutrient database 1260 according to an exemplary embodiment of the present invention. The life goal database 1260 according to the present embodiment holds the life goal ID and the amount of each nutrient to be added corresponding to the life goal ID.

The amount of each nutrient to be added is represented as a ratio to the required amount of the nutrient per a day. For example, in case of the life goal ID 3, i.e., the countermeasure against skin problems, it is shown that the nutrient ID 1 (Vitamin A) is added by 100% of the required amount of Vitamin A per a day, the nutrient ID 2 (Vitamin D) by 0% of the required amount of Vitamin D per a day, the nutrient ID 20

(calcium) by 100% of the required amount of calcium per a day and the nutrient ID 21 (magnesium) by 100% of the required amount of magnesium per a day.

FIG. 11 shows an example of a presumed disease name database 1280 according to an exemplary embodiment of the present invention. The presumed disease name database 1280 according to the present embodiment holds the information indicating the presumption condition consisting of the response to the medical inquiry and the nutritional condition, the presumed disease name and the medical department.

The disease name presuming unit 1110 outputs the presumed disease name of the line satisfying the presumption condition, if the presumption condition in the presumed disease name database 1280 is satisfied. For example, the first line of FIG. 11 indicates that the response to "Do you feel dizzy?" of the medical inquiry ID 3109 is "Yes", the response to "Have you taken in the previous nutritional supplement?" of the medical inquiry ID 4000 is "Yes" and the nutrient ID 5 (Vitamin B1), the nutrient ID 6 (Vitamin B2), the nutrient ID 7 (niacin), the nutrient ID 8 (pantothenic acid) and the nutrient ID 15 (iron) are sufficient in relation to the insufficient degree of nutrient stored in the medical inquiry history database 1230. The disease name presuming unit 1110 judges whether the presumption condition is satisfied or not based on the response to the medical inquiry of the customer and the contents of the medical inquiry history database 1230, and judges the disease name as Vertigo in case the presumption condition is satisfied. In addition, at this time, the disease name presuming unit 1110 obtains otolaryngology or neurosurgery suitable for treating "vertigo" as the medical department.

FIG. 12 shows an example of a medical institution database 1290 according to an exemplary embodiment of the present invention. The medical institution database 1290 according to the present embodiment holds the information indicating the name of the medical institution, the medical department, the address and the contact place (destination).

The medical institution recommending unit 1120 searches the medical institution database 1290 taking the address of the customer and the medical department outputted by the disease name presuming unit 1110 as a key. In addition, the medical institution recommending unit 1120 acquires the approximate address and the medical institution capable of treating the disease of the presumed name.

FIG. 13 shows an example of a correlation database 1270 according to an exemplary embodiment of the present invention. The correlation database 1270 according to the present embodiment holds the correlation ID, the condition corresponding to the correlation ID and the insufficient nutrient.

The correlation processing unit 1040 analyzes the correlation between the condition relating to the living environment or the life goal and the insufficient degree of nutrient based on the data in the personal information database 1200 and/or the medical inquiry history database 1230. And, the correlation processing unit 1040 registers the combination of the correlation ID, the condition and the insufficient nutrient into the correlation database 1270, which are assigned anew, in case there is the correlation between the result condition of analysis and the insufficient degree of nutrient.

Figure 14:
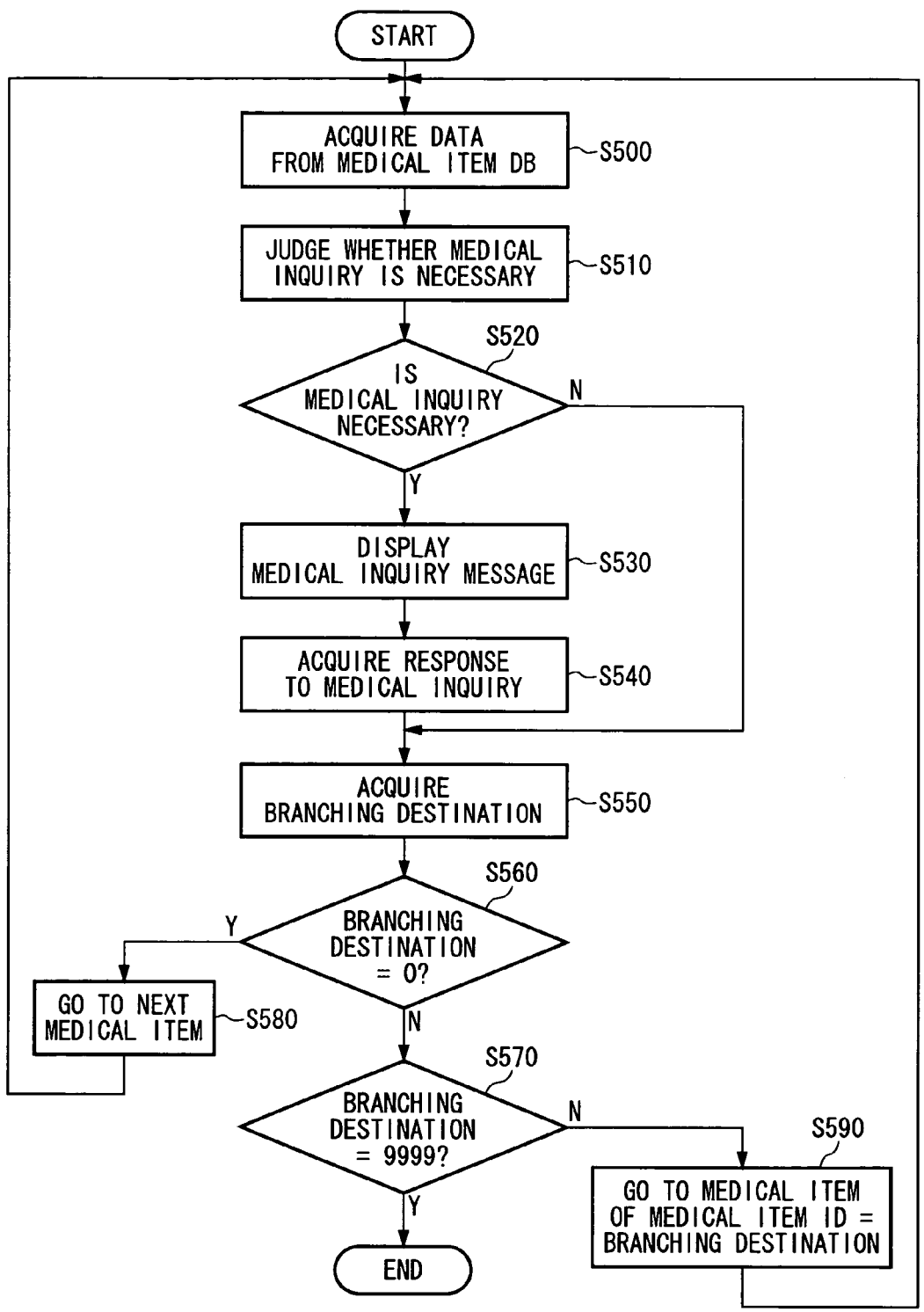
FIG. 14 is a flowchart that shows a medical inquiry process of a medical inquiry processing unit 1020 according to an exemplary embodiment of the present invention.

FIG. 14 is a flowchart that shows a medical inquiry process of a medical inquiry processing unit 1020 according to an exemplary embodiment of the present invention. The medical inquiry processing unit 1020 begins the medical inquiry from the medical inquiry ID 1000, the first medical inquiry item.

First, the medical inquiry processing unit 1020 acquires the data of line corresponding to the medical inquiry ID to be processed from the medical inquiry item database 1210 (S500).

Then, the medical inquiry processing unit 1020 judges whether to perform the medical inquiry of the medical inquiry item corresponding to the medical inquiry ID to be processed (S510). That is, the medical inquiry processing unit 1020 judges whether the medical inquiry is necessary by judging each condition of the medical inquiry designation for a step, the medical inquiry designation for a life goal, the medical inquiry interval, the medical inquiry designation for an insufficient nutrient and the correlation in the correlation database 1270.

The medical inquiry processing unit 1020 extracts the line in which the personal information and the data in the medical inquiry history database 1230 relating to the customer matches the condition registered in the correlation database 1270 during judging whether the medical inquiry by the correlation is necessary. And, the medical inquiry processing unit 1020 considers that the insufficient nutrient held in the line is insufficient to the customer in processing, and judges the condition of the medical inquiry of an insufficient nutrient.

Next, the medical inquiry processing unit 1020 proceeds with the process of the step S550 in case of judging the medical inquiry is not necessary in the step S510 (S520).

Then, the medical inquiry processing unit 1020 displays the medical inquiry message and the response field to the terminal 1000 of the customer via the network 1001 (S530).

Then, the medical inquiry processing unit 1020 acquires the response to the medical inquiry from the terminal 1000 of the customer via the network 1001 (S540).

Then, the medical inquiry processing unit 1020 acquires the medical inquiry ID of the branching destination corresponding to the response to the medical inquiry from the branching destination for a response in regard to the medical inquiry item in processing (S550).

Then, the medical inquiry processing unit 1020 checks whether the medical inquiry ID of the branching destination is "0" or not (S560). If the medical inquiry ID of the branching destination is "0", the medical inquiry processing unit 1020 carries out the process of the medical inquiry item of the next line (S580), and proceeds to go to the step S500.

Next, the medical inquiry processing unit 1020 checks whether the medical inquiry ID of the branching destination is "9999" or not (S570). If the medical inquiry ID of the branching destination is not "9999", the medical inquiry processing unit 1020 carries out the process of the medical inquiry item designated by the medical inquiry ID of the branching destination (S590), and proceeds to go to the step S500. If the medical inquiry ID of the branching destination is "9999", the medical inquiry processing unit 1020 finishes the medical inquiry process.

By the processes above, it is possible to perform the medical inquiry using the different medical inquiry item corresponding to the response to the medical inquiry. For example, in case the customer responses "Yes" to the medical inquiry ID 2002 in FIG. 5, the medical inquiry processing unit 1020 proceeds with processes in an order of the medical inquiry ID 2003 and then the medical inquiry ID 3000. In case the customer responses "rather Yes" or "No" to the medical inquiry ID 2002, the medical inquiry processing unit 1020 proceeds with processes in an order of the medical inquiry ID 2100, the medical inquiry ID 2104 and then the medical inquiry ID 3000. In addition, for example, in case the customer responses "No" to the medical inquiry ID 3000, the medical inquiry processing unit 1020 proceeds with the process of the medical inquiry ID 4000 without performing the medical inquiry in an order of the medical inquiry ID 3100, the medical inquiry ID 3108 and then the medical inquiry ID 3109.

In addition, the medical inquiry processing unit 1020 can obtain the response to the medical inquiry of the customer in regard to the medical inquiry item relating to the nutrient liable to be insufficient statistically based on the correlation by judging whether to perform the medical inquiry based on the correlation in the step S510.

Figure 15:
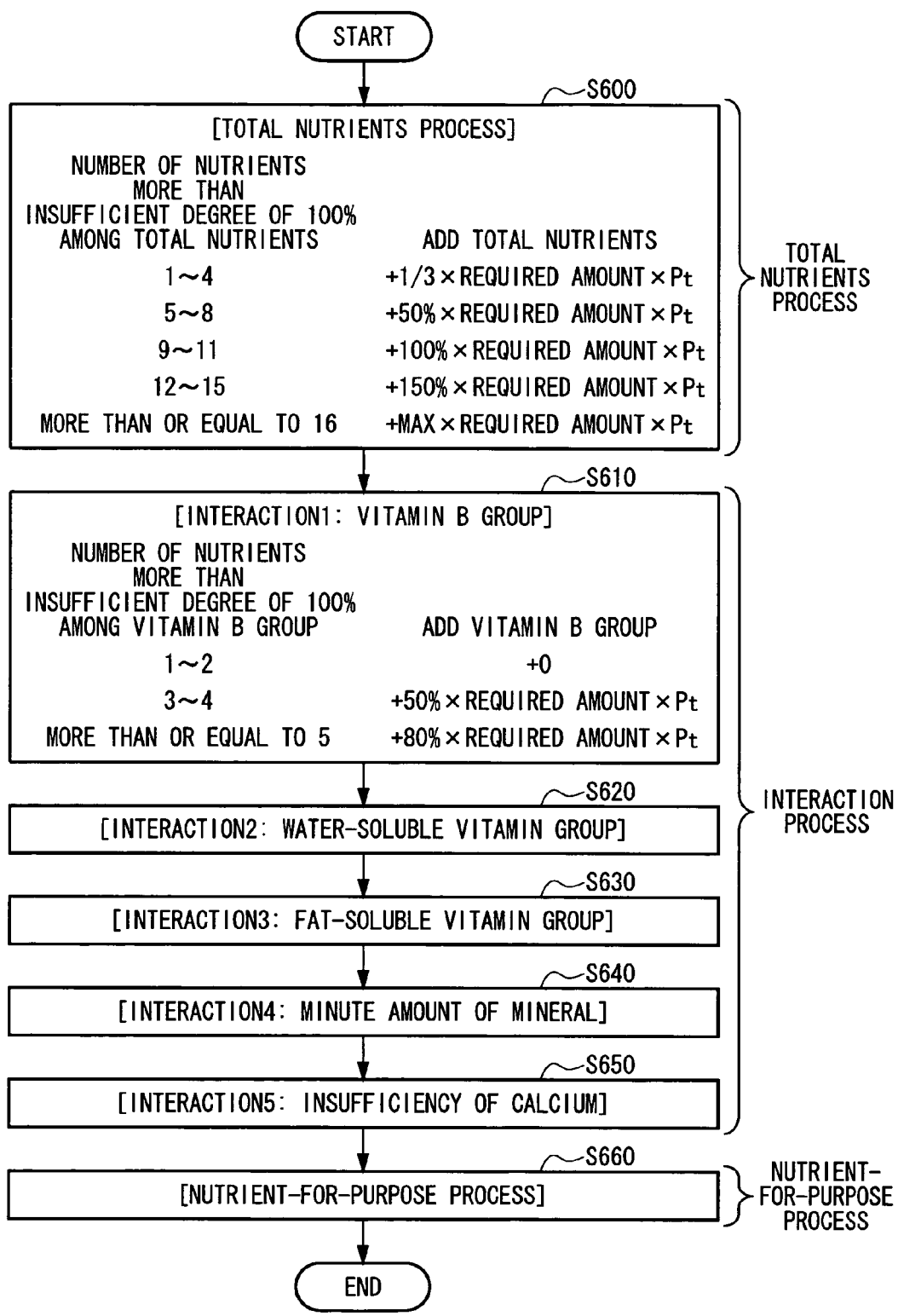
FIG. 15 is a flowchart that shows a total nutrient process, an interaction process and a nutrient-for-purpose process of a nutrient amount processing unit 1050 according to an exemplary embodiment of the present invention.

FIG. 15 is a flowchart that shows a total nutrient process, an interaction process and a nutrient-for-purpose process of a nutrient amount processing unit 1050 according to an exemplary embodiment of the present invention. The total nutrients processing unit 1070 calculates the insufficient degree for each nutrient using the medical inquiry response database 1220 based on the response to the medical inquiry, before calculating the nutrient requirement amount of the customer. And, the nutrient amount processing unit 1050 performs the total nutrient process, the interaction process and the nutrient-for-purpose process taking this insufficient degree as the initial value of the nutrient requirement amount.

First, the total nutrients processing unit 1070 performs a general process of adding total nutrients to the nutrient requirement amount with a constant ratio corresponding to the number of nutrients of which the insufficient degree is more than 100% (S600). In the present embodiment, if the number of nutrients, of which the insufficient degree is more than 100%, is 1 to 4 among the total 21 nutrients, the total nutrients processing unit 1070 adds the portion of ⅓ of the required amount per a day multiplied by the ratio Pt to the nutrient requirement amount in regard to the total nutrients. Although the number of nutrients, of which the insufficient degree is more than 100%, is more than 5, it adds the total nutrients to the nutrient requirement amount as shown in the block of the step S600.

Here, Pt, a value indicating the proportion of the nutrient amount to be added in the total nutrient process and the interaction process, is, for example, the value of 1 in the first step, 0.5 in the second step, 0.25 in the third step and 0 in the fourth and fifth steps. By reducing Pt in each step gradually, the blending system of a nutritional supplement 1002 can be realized, wherein it suggests the nutritional supplement to add nutrients for the customer in an integrated manner at the beginning and suggests the nutritional supplement to add nutrients necessary to achieve the life goal and nutrients liable to be insufficient to the customer gradually.

Next, the interaction processing unit 1080 performs the interaction process of adding the total nutrients of Vitamin B group with a constant ratio corresponding to the number of nutrients, of which the insufficient degree is more than 100% among the Vitamin B group (the nutrient ID=5 to 12) (S610). In the present embodiment, if the number of the nutrient of which the insufficient degree is more than 100% is 3 or 4 among 8 of the vitamin B group, the interaction processing unit 1080 adds the portion of 50% of the required amount per a day multiplied by the ratio Pt to the nutrient requirement amount in regard to the nutrients of Vitamin B group. Although the number of nutrients, of which the insufficient degree is more than 100%, is more than 5, it adds the Vitamin B group to the nutrient requirement amount as shown in the block of the step S610.

Next, the interaction processing unit 1080 performs the interaction process in regard to the water-soluble Vitamin group (the nutrient ID=5 to 14) (S620).

Next, the interaction processing unit 1080 performs the interaction process in regard to the fat-soluble Vitamin group (the nutrient ID=1 to 4) (S630).

Next, the interaction processing unit 1080 performs the interaction process in regard to the minute portion of mineral (the nutrient ID=15 to 21) (S640). In the steps S620 to S640 above, the interaction processing unit 1080 adjusts the nutrient requirement amount by using the same method as that of the case of the Vitamin B group.

Next, the interaction processing unit 1080 performs the interaction process corresponding to the insufficiency of calcium (S650). That is, if the insufficient degree of calcium (the nutrient ID 20) is more than 200%, the interaction processing unit 1080 adds magnesium (the nutrient ID21), Vitamin D (the nutrient ID2) and Vitamin K (the nutrient ID4), which help to absorb calcium, to the nutrient requirement amount. The amount to be added is set to be, for example, the portion of ⅓ of the required amount per a day multiplied by the ratio Pt in case at least two of magnesium, Vitamin D and Vitamin K wherein the insufficient degree is more than 100%, the portion of 100% of the required amount per a day multiplied by the ratio Pt in case at least two of magnesium, Vitamin D and Vitamin K wherein the insufficient degree is more than 100% and less than or equal to 150% and a predetermined maximum amount multiplied by the ratio Pt in case at least two of magnesium, Vitamin D and Vitamin K wherein the insufficient degree is more than 150%.

Next, the nutrient-for-purpose processing unit 1090 performs the nutrient-for-purpose process to add nutrients corresponding to the life goal (S660). In other words, the nutrient-for-purpose processing unit 1090 acquires the amount of each nutrient to be added by searching the life goal database 1260 shown in FIG. 10 taking the life goal of the customer as a key and adds it to the nutrient requirement amount.

Figure 16:
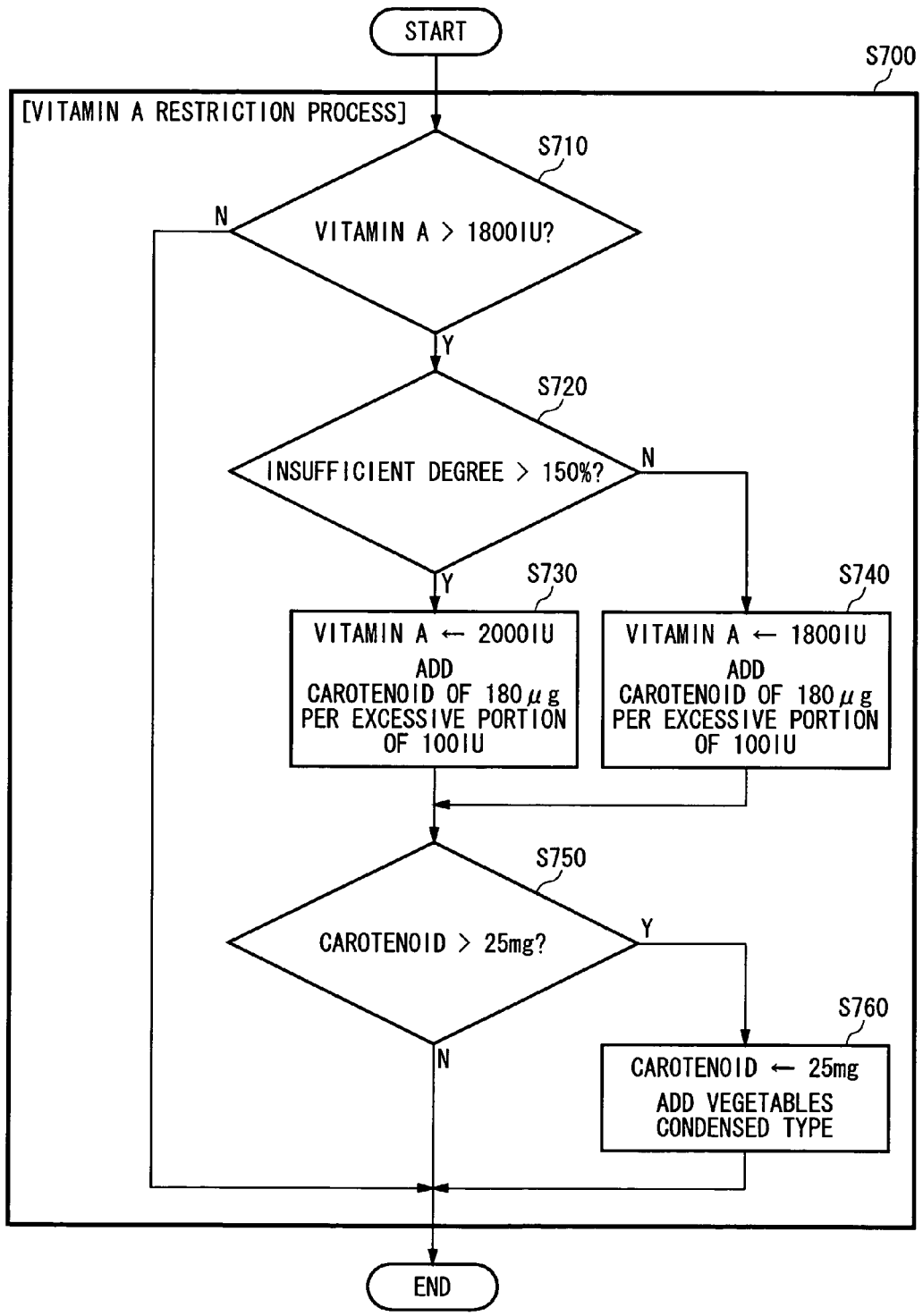
FIG. 16 is a flowchart that shows a restriction process of a nutrient amount processing unit 1050 according to an exemplary embodiment of the present invention.

FIG. 16 is a flowchart that shows a restriction process of a restriction processing unit 1100 according to an exemplary embodiment of the present invention. The restriction processing unit 1100 performs the restriction process based on the required amount of each nutrient per a day and the upper limit ingestion amount held by the nutrient database 1240. FIG. 16 shows the restriction process of Vitamin A for a woman of age 18 to 29.

The restriction processing unit 1100 searches the nutrient database 1240 taking the sex, the age of the customer and the nutrient ID1 (Vitamin A) as a key and acquires the required amount 1800IU and the upper limit ingestion amount 5000IU per a day, before the restriction process of Vitamin A.

In the restriction process of Vitamin A (S700), the restriction processing unit 1100 compares the nutrient requirement amount of Vitamin A received from the nutrient-for-purpose processing unit 1090 with the required amount 1800IU per a day (S710). If the nutrient requirement amount of Vitamin A is less than 1800IU, the restriction processing unit 1100 finishes the restriction process of Vitamin A because the restriction process of Vitamin A is not necessary.

Next, the restriction processing unit 1100 checks whether the insufficient degree of Vitamin A calculated by the total nutrients processing unit 1070 based on the response to the medical inquiry is more than 150% or not (S720).

If the insufficient degree of Vitamin A is more than 150%, the restriction processing unit 1100 restricts the nutrient requirement amount of Vitamin A to 2000IU. At this time, the restriction processing unit 1100 adds carotenoid of 180 μg to the nutrient requirement amount per the excessive amount of 100IU for the portion wherein the original nutrient requirement amount of Vitamin A is more than 2000IU (S730).

Therefore, it is possible to restrict the content of Vitamin A in order to provide it as a nutritional supplement, and to make up for the insufficiency by adding carotenoid changeable into Vitamin A in the body if necessary.

If the insufficient degree of Vitamin A is more than 150%, the restriction processing unit 1100 restricts the nutrient requirement amount of Vitamin A to 1800IU. At this time, the restriction processing unit 1100 adds carotenoid of 180 μg to the nutrient requirement amount per the excessive amount of 100IU for the portion wherein the original nutrient requirement amount of Vitamin A is more than 1800IU (S740).

Next, the restriction processing unit 1100 checks whether the amount of added carotenoid is more than 25 mg or not (S750). If the amount of added carotenoid is more than 25 mg, the restriction processing unit 1100 restricts the amount of carotenoid to be added to 25 mg, and allows the nutritional supplement suggesting unit 1130 to suggest to the customer that he or she eats nutritional food condensed with vegetables together with the nutritional supplement (S760).

Figure 17:
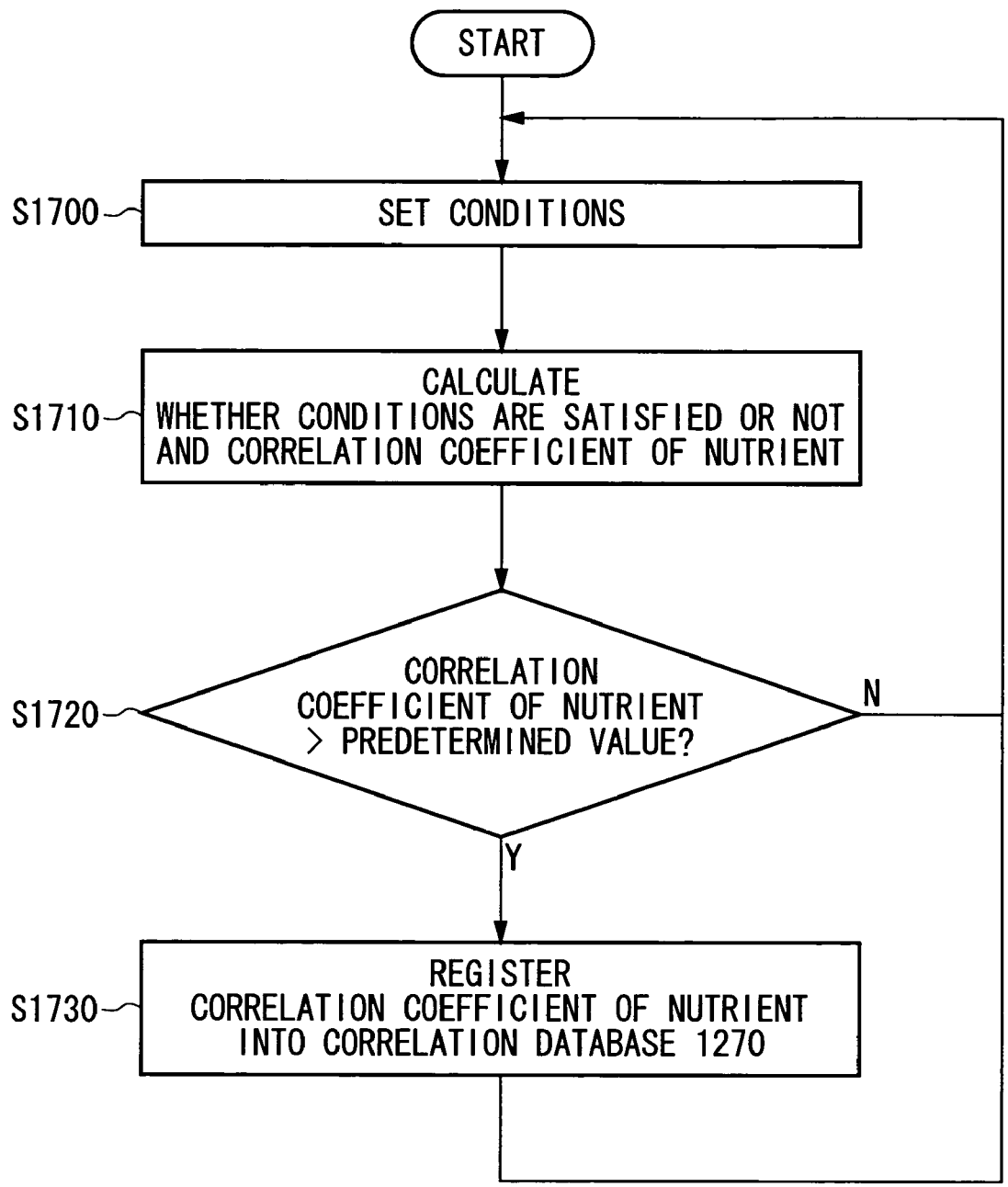
FIG. 17 is a flowchart that shows a correlation process of a correlation processing unit 1040 according to an exemplary embodiment of the present invention.

FIG. 17 is a flowchart that shows a correlation process of a correlation processing unit 1040 according to an exemplary embodiment of the present invention. In the present embodiment, the correlation processing unit 1040 analyzes the correlation between the living environment or the life goal and the insufficient degree of nutrient by using the data in the medical inquiry history database 1230 and/or the personal information database 1200.

First, the correlation processing unit 1040 sets the condition that is the object of analyzing whether there is any correlation (S1700). The condition may be the response to the medical inquiry such as drinking, smoking, or the like held by the medical inquiry history database 1230, e.g., whether the address is Tokyo or not in the personal information database 1200.

In addition, the correlation processing unit 1040 may set a composite condition from the medical inquiry history database 1230 and/or the personal information database 1200 such as a smoker living in Tokyo.

Alternatively, the correlation processing unit 1040 may set the condition by using the passage of time of the response to the medical inquiry of the customer in the medical inquiry history database 1230. For example, the correlation processing unit 1040 can analyze the correlation between the condition of whether the weight is reduced or not in the medical inquiry history database 1230 and the insufficient degree of nutrient by using the response to the medical inquiry relating to the weight.

Next, the correlation processing unit 1040 calculates the correlation coefficient between the condition and the insufficient degree of nutrient by using the insufficient degree of nutrient satisfying the condition and the insufficient degree of nutrient not satisfying the condition for each nutrient (S1710).

That is, the correlation processing unit 1040 first examines the personal information database 1200 and the line of the medical inquiry history database 1230 having the corresponding customer ID for each customer in the personal information database 1200, and judges whether the condition of the customer is satisfied or not.

Next, the correlation processing unit 1040 searches the insufficient degree of nutrient from the medical inquiry history database 1230 by using the customer ID, the nutrient ID of the nutrient to be analyzed and the kind of history, which is "the insufficient degree". Further, the correlation processing unit 1040 performs the process of acquiring the new insufficient degree or acquiring the change of the insufficient degree with reference to the registration data.

And, the correlation processing unit 1040 calculates the correlation coefficient by using whether the condition is satisfied or not and the insufficient degree of nutrient.

The correlation processing unit 1040 performs the processes above on each nutrient to obtain the correlation between the condition and the insufficient degree of nutrient.

Next, the correlation processing unit 1040 judges whether the correlation coefficient corresponding to each nutrient is more than a predetermined value or not. And, the correlation processing unit 1040 proceeds with the process of the step S1700 to perform analysis for the next condition, in case each correlation coefficient corresponding to the all of the nutrients is more than the predetermined value (S1720).

Next, the correlation processing unit 1040 registers the correlation analyzed into the correlation database 1270 (S1730). That is, the correlation processing unit 1040 adds a line to the correlation database 1270 by assigning new correlation ID to register the condition into the line. In addition, it checks the table of the nutrient ID corresponding to the insufficient nutrient (presumed) in regard to the nutrient of the correlation coefficient is more than the predetermined value.

As described above, the correlation processing unit 1040 analyzes the relation between the condition and the insufficient degree of nutrient while changing the condition all the way. Therefore, the blending system of a nutritional supplement 1002 analyzes the correlation between the living environment or the life goal and the insufficient degree of nutrient based on the personal information of the customer and the medical inquiry history accumulated, so that it can select the medical inquiry item based on the analysis result.

Figure 18:
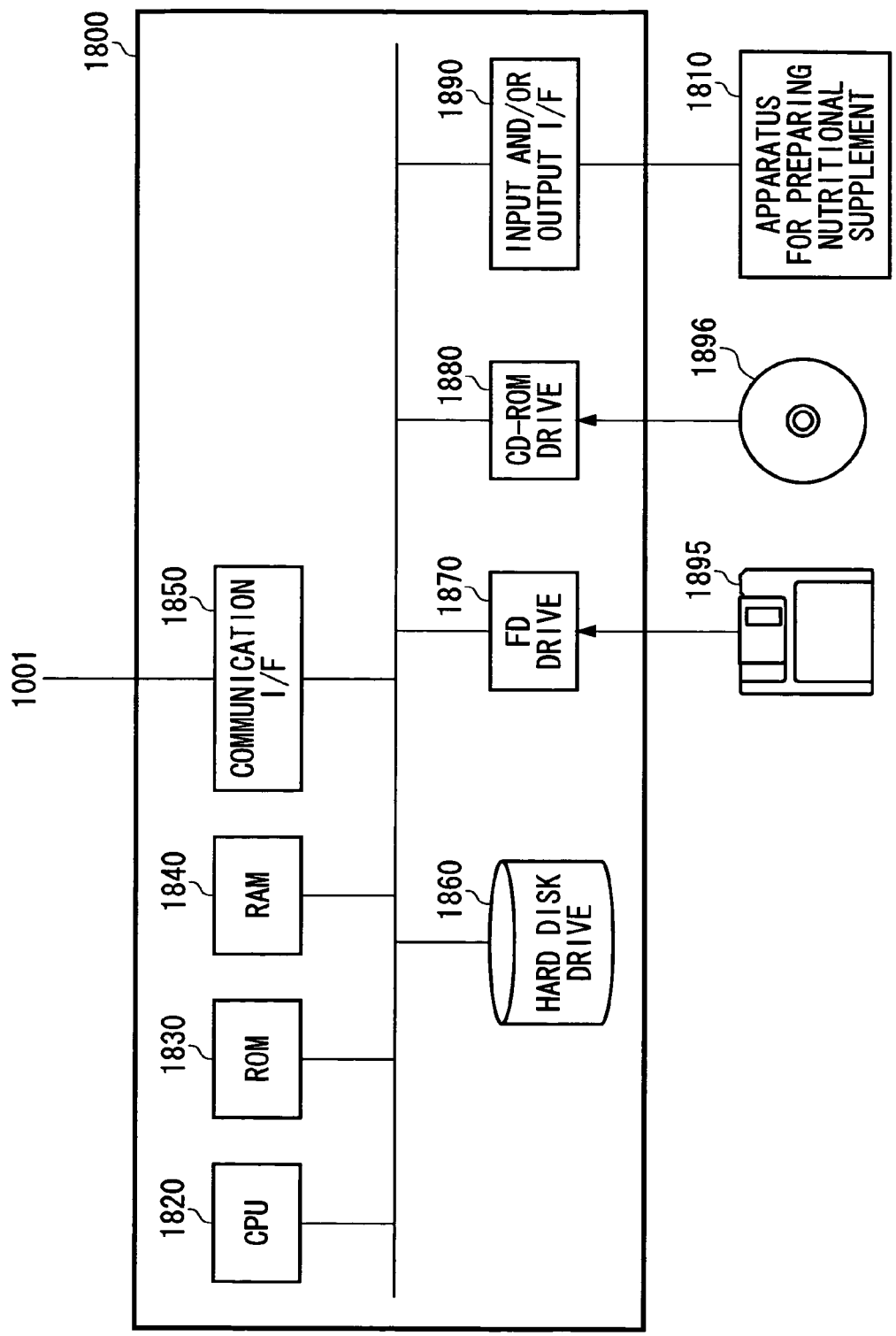
FIG. 18 shows an example of the hardware configuration of a blending system of a nutritional supplement 1002 according to an exemplary embodiment of the present invention.

FIG. 18 shows an example of the hardware configuration of a blending system of a nutritional supplement 1002 according to an exemplary embodiment of the present invention. The functions of the blending system of a nutritional supplement 1002 shown in FIG. 2 may be realized by the cooperation of a calculator 1800 including a CPU 1820, a ROM 1830, a RAM 1840, a communication interface 1850, a hard disc drive 1860 and an input and/or output interface 1890, an apparatus for preparing a nutritional supplement 1810 and a program executed in the calculator 1800.

The program includes the function to allow the calculator 1800 and the apparatus for preparing a nutritional supplement 1810 to operate as the customer authenticating unit 1010, the medical inquiry processing unit 1020, the environment searching unit 1025, the correlation processing unit 1040, the total nutrients processing unit 1070, the interaction processing unit 1080, the nutrient-for-purpose processing unit 1090, the restriction processing unit 1100, the disease name presuming unit 1110, the medical institution recommending unit 1120, the nutritional supplement suggesting unit 1130, the preparation request inputting unit 1140 and the nutritional supplement blending unit 1150. Here, the function of the nutritional supplement blending unit 1150 may be realized by the combination of a program for controlling the apparatus for preparing a nutritional supplement 1810 operating in the calculator 1800 and the apparatus for preparing a nutritional supplement 1810.

In addition, the personal information database 1200, the medical inquiry item database 1210, the medical inquiry response database 1220, the medical inquiry history database 1230, the nutrient database 1240, the living environment database 1250, the life goal database 1260, the correlation database 1270, the presumed disease name database 1280 and the medical institution database 1290 is placed in the hard disc drive of the calculator 1800.

The programs and/or databases above may be stored in an external recording medium. The recording medium may be not only a floppy disc 1895 or a CD-ROM 1896, but also an optical recording medium such as a DVD, a magnetic recording medium such as an MD, a magnetooptical recording medium such as a PD, a tape recording medium, a semiconductor memory such as an IC card or the like. In addition, a memory such as a hard disc or a RAM provided in a server system connected to a dedicated communication network or the Internet may be used as the recording medium to provide the programs and/or databases to the blending system of a nutritional supplement 1002 via the communication network.

The recording medium above is used only for realizing the blending system of a nutritional supplement 1002, and thus it is obvious that manufacturing, selling and/or the like of the recording medium above commercially should infringe the patent right based on the present application.

In addition, the blending system of a nutritional supplement 1002 shown in FIG. 2 may be realized by using a plurality of the calculators. In this case, each part, controls the nutritional supplement preparing apparatus, of the customer authenticating unit 1010, the medical inquiry processing unit 1020, the environment searching unit 1025, the correlation processing unit 1040, the total nutrients processing unit 1070, the interaction processing unit 1080, the nutrient-for-purpose processing unit 1090, the restriction processing unit 1100, the disease name presuming unit 1110, the medical institution recommending unit 1120, the nutritional supplement suggesting unit 1130, the preparation request inputting unit 1140 and the nutritional supplement blending unit 1150 and the data of the personal information database 1200, the medical inquiry item database 1210, the medical inquiry response database 1220, the medical inquiry history database 1230, the nutrient database 1240, the living environment database 1250, the life goal database 1260, the correlation database 1270, the presumed disease name database 1280 and the medical institution database 1290 may be positioned at certain place of a plurality of the calculators.

Figure 19:
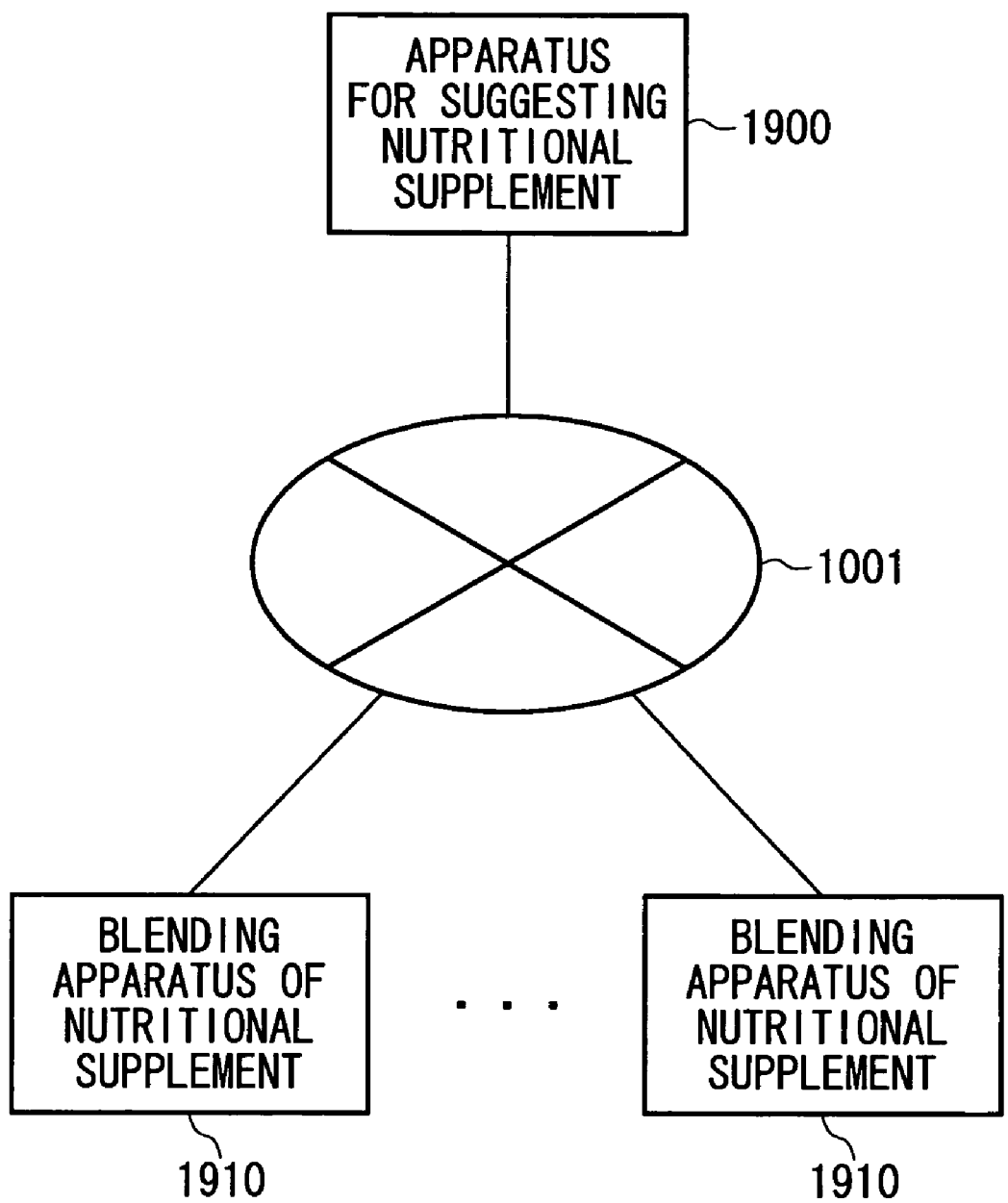
FIG. 19 shows an example of a blending system of a nutritional supplement 1002 according to an alternatively exemplary embodiment of the present invention.

FIG. 19 shows an example of a blending system of a nutritional supplement 1002 according to an alternatively exemplary embodiment of the present invention. The blending system of a nutritional supplement 1002 has a configuration wherein an apparatus for suggesting a nutritional supplement 1900 is connected to at least one blending apparatus of a nutritional supplement 1910 via a network 1001. The apparatus for suggesting a nutritional supplement 1900 may be placed at, e.g., a drugstore, a convenience store or the like.

The apparatus for suggesting a nutritional supplement 1900 and the blending apparatus of a nutritional supplement 1910 share the functions of the blending system of a nutritional supplement 1002 shown in FIG. 2.

Figure 20:
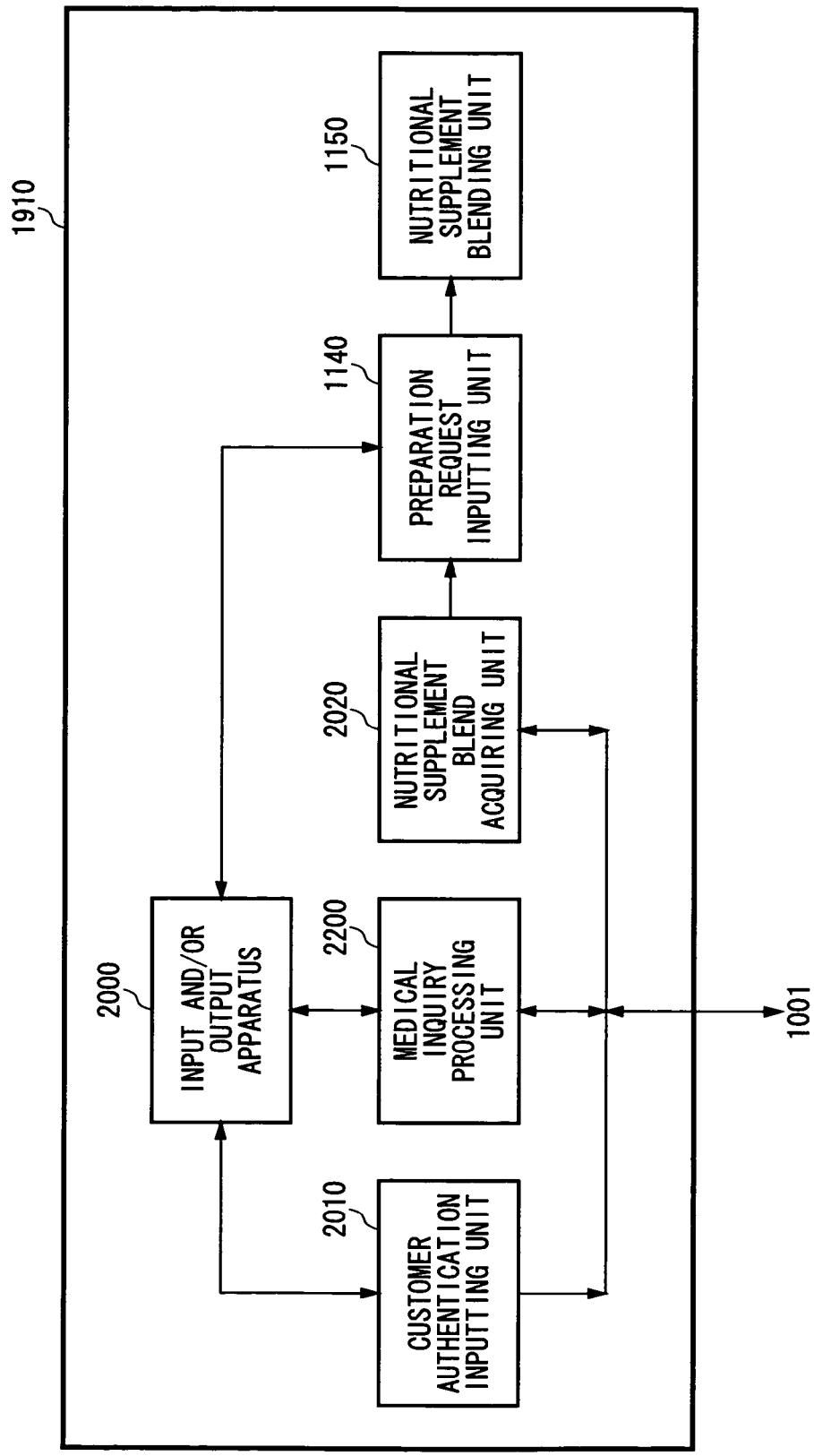
FIG. 20 shows an example of a blending apparatus of a nutritional supplement 1910 according to an alternatively exemplary embodiment of the present invention.

FIG. 20 shows an example of a blending apparatus of a nutritional supplement 1910 according to an alternatively exemplary embodiment of the present invention. The blending apparatus of a nutritional supplement 1910 includes an input-output apparatus 2000, a medical inquiry processing unit 2200, a customer authentication inputting unit 2010, a nutritional supplement blend acquiring unit 2020, a preparation request inputting unit 1140 and a nutritional supplement blending unit 1150.

The combination of input-output apparatus 2000 and the customer authentication inputting unit 2010 is an example of the customer authentication inputting unit according to the present invention.

The input-output apparatus 2000 performs the input and/or output process to the customer such as the authentication input of the customer, the display of the medical inquiry item and the input of the response to the medical inquiry and the suggestion of the blend of the nutritional supplement and the input of the preparation request.

The customer authentication inputting unit 2010 performs the authentication of the customer to the apparatus for suggesting a nutritional supplement 1900 via the network 1001 by using the authentication information of the customer obtained using the input-output apparatus 2000. The medical inquiry processing unit 2200 acquires the medical inquiry item from the apparatus for suggesting a nutritional supplement 1900 via the network 1001, and obtains the response to the medical inquiry from the customer while displaying the medical inquiry item by using the input-output apparatus 2000. And, the medical inquiry processing unit 2200 sends the response to the medical inquiry acquired to the apparatus for suggesting a nutritional supplement 1900.

The apparatus for suggesting a nutritional supplement 1900 suggests the blend of the nutritional supplement based on the response to the medical inquiry received from the medical inquiry processing unit 2200 of the blending apparatus of a nutritional supplement 1910 and the data in the apparatus for suggesting a nutritional supplement 1900.

The nutritional supplement blend acquiring unit 2020 acquires the blend of the nutritional supplement suggested by the apparatus for suggesting a nutritional supplement 1900 via the network 1001.

The preparation request inputting unit 1140 checks if the customer requests the preparation of the nutritional supplement based on the blend information received from the nutritional supplement blend acquiring unit 2020 via the input-output apparatus 2000.

In addition, the preparation request inputting unit 1140 may record the blend information received from the nutritional supplement blend acquiring unit 2020 to a magnetic card, an IC card, a flash memory or the like via the input-output apparatus 2000.

The nutritional supplement blending unit 1150 receives the blend information acquired by the nutritional supplement blend acquiring unit 2020 via the preparation request inputting unit 1140 and blends nutrients for the nutritional supplement.

Figure 21:
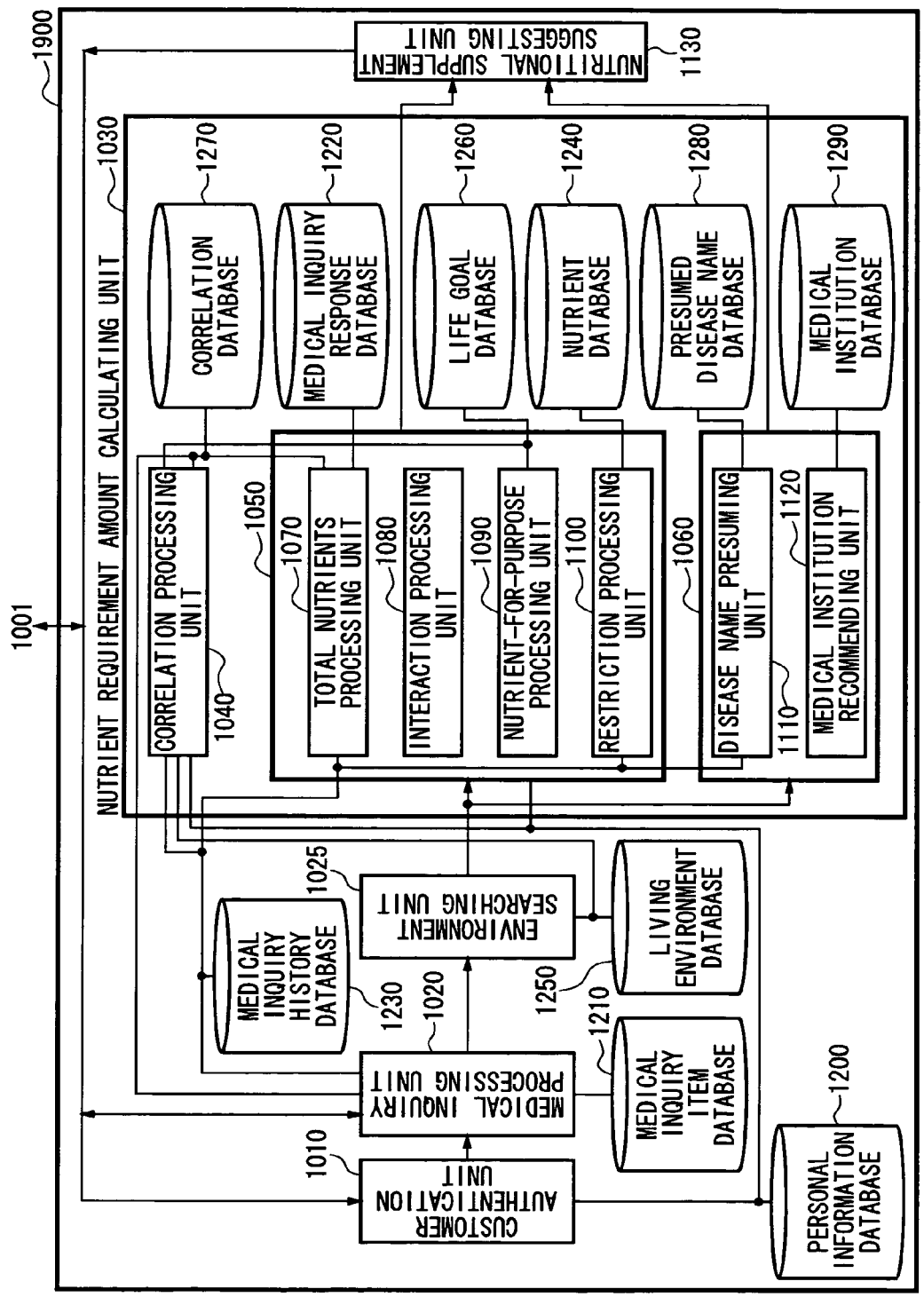
FIG. 21 shows an example of an apparatus for suggesting a nutritional supplement 1900 according to an alternatively exemplary embodiment of the present invention.

FIG. 21 shows an example of an apparatus for suggesting a nutritional supplement 1900 according to an alternatively exemplary embodiment of the present invention. The apparatus for suggesting a nutritional supplement 1900 is different from the blending system of a nutritional supplement 1002 shown in FIG. 2 in that the preparation request inputting unit 1140 and the nutritional supplement blending unit 1150 included in the blending apparatus of a nutritional supplement shown in FIG. 2 are removed and that the blend of the nutritional supplement is sent from the nutritional supplement suggesting unit 1130 to the nutritional supplement blend acquiring unit 2020 of the nutritional supplement blending unit 1910 via the network 1001.

The customer authenticating unit 1010 obtains the authentication information of the customer from the blending apparatus of a nutritional supplement 1910 to perform the authentication of the customer. The medical inquiry processing unit 1020 obtains the response to the medical inquiry of the customer from the input-output apparatus 2000 of the blending apparatus of a nutritional supplement 1910 via the network 1001. The apparatus for suggesting a nutritional supplement 1900 hereafter suggests the blend of the nutritional supplement like the blending system of a nutritional supplement shown in FIG. 2 and sends the blend of the nutritional supplement to the nutritional supplement blend acquiring unit 2020 of the nutritional supplement blending unit 1910 via the network 1001.

The apparatus for suggesting a nutritional supplement 1900 may adopt a method of performing the medical inquiry in response to the access received from the blending apparatus of a nutritional supplement 1910. That is, for example, when the customer authenticating unit 1010 performs the authentication of the customer, the apparatus for suggesting a nutritional supplement 1900 suggests the blend of the nutritional supplement based on the insufficient degree of nutrient of the customer or the data about the blend of the nutritional supplement held by the medical inquiry history database 1230. Therefore, the blending apparatus of a nutritional supplement 1910 can blend nutrients for the nutritional supplement, even though it does not have the function of displaying the medical inquiry item on the input-output apparatus 2000 and performing the input of the response to the medical inquiry.

Figure 22:
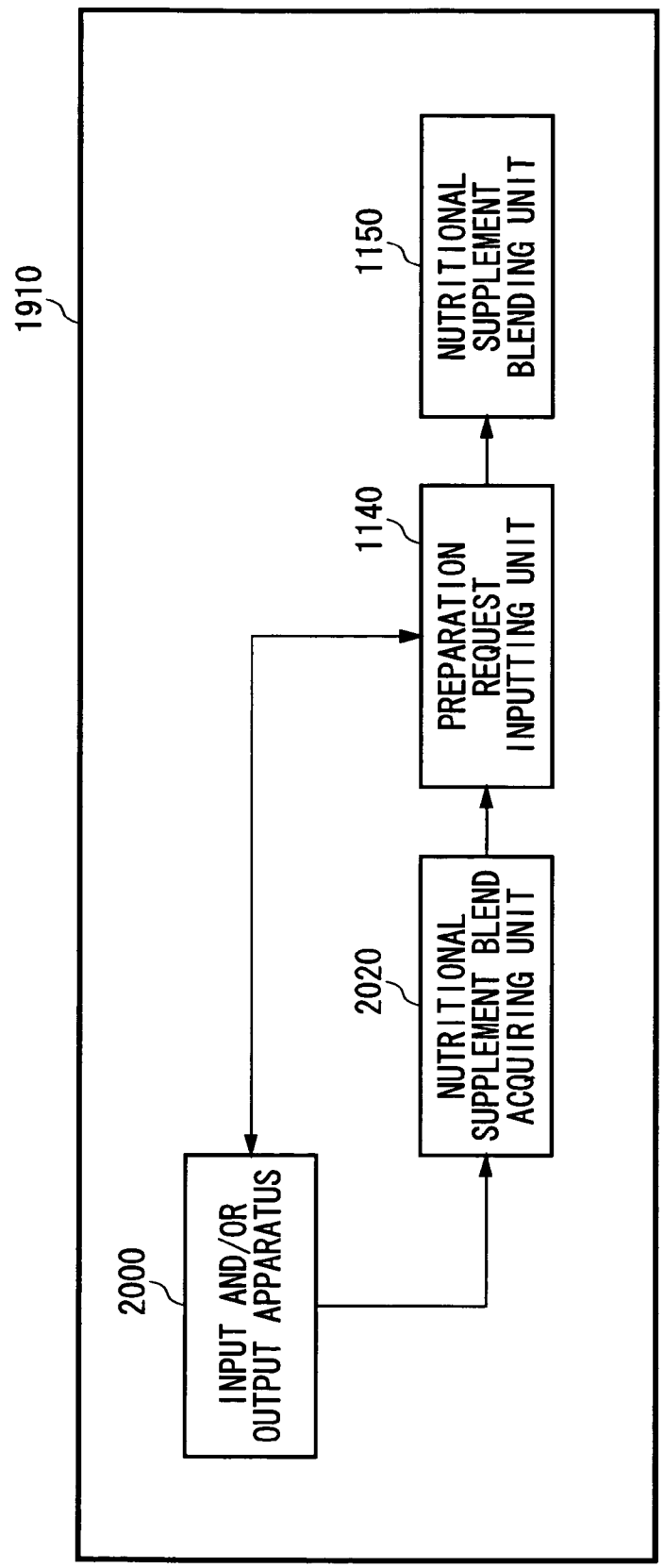
FIG. 22 shows an example of a blending apparatus of a nutritional supplement 1910 according to another alternatively exemplary embodiment of the present invention.

FIG. 22 shows an example of a blending apparatus of a nutritional supplement 1910 according to another alternatively exemplary embodiment of the present invention. The blending apparatus of a nutritional supplement 1910 includes an input-output apparatus 2000, a nutritional supplement blend acquiring unit 2020, a preparation request inputting unit 1140 and a nutritional supplement blending unit 1150.

The combination of the input-output apparatus 2000 and the nutritional supplement blend acquiring unit 2020 is an example of the nutritional supplement blend acquiring unit according to the present invention.

The input-output apparatus 2000 performs the input and/or output process from or to the customer such as the input of the blend information about the nutritional supplement for the customer and the input of the preparation request. Here, the input-output apparatus 2000 may acquire the blend information of the nutritional supplement from the terminal 1000 of FIG. 1 or the magnetic card, the IC card, the flash memory or the like to which the blend information is recorded by the input-output apparatus 2000 of FIG. 20.

The nutritional supplement blend acquiring unit 2020 acquires the blend of the nutritional supplement for the customer from the input-output apparatus 2000.

The preparation request inputting unit 1140 checks if the customer requests the preparation of the nutritional supplement based on the blend information received from the nutritional supplement blend acquiring unit 2020 via the input-output apparatus 2000.

The nutritional supplement blending unit 1150 receives the blend information acquired by the nutritional supplement blend acquiring unit 2020 via the preparation request inputting unit 1140 and blends the nutritional supplement.

In the exemplary embodiment and the alternatively exemplary embodiment above, the blending system of a nutritional supplement 1002 can calculate the nutrient requirement amount of the customer based on the result of the medical inquiry performed on the customer in an integrated manner at a different time. In addition, the blending system of a nutritional supplement 1002 can suggest the nutritional supplement suitable for the customer based on the nutrient requirement amount calculated. Further, the blending system of a nutritional supplement 1002 can provide the nutritional supplement prepared to the customer by receiving the preparation request of the suggested nutritional supplement from the customer.

Accordingly, the blending system of a nutritional supplement 1002 can provide a service to support nutrient ingestion corresponding to the constitution or the life goal of the customer.

Although the present invention has been described by way of exemplary embodiments, it should be understood that those skilled in the art might make many changes and substitutions without departing from the spirit and the scope of the present invention, which is defined only by the appended claims.

For example, the nutrient requirement amount calculating unit 1030 may be used independently as the apparatus for calculating the nutrient requirement amount of the customer based on the response to the medical inquiry. Further, the apparatus for calculating nutrient requirement amount may further include the medical inquiry processing unit 1020 and/or the environment searching unit 1025. In addition, the nutrient amount processing unit 1050 may suggest the nutrient requirement amount to he customer and may include the function of advising the customer on nutrient ingestion based on the insufficient degree of nutrient of the customer.

In addition, the nutrient requirement amount calculating unit 1030 and the nutritional supplement suggesting unit 1130 may be used independently as the apparatus for suggesting the blend of a nutritional supplement by calculating the nutrient requirement amount of the customer from the response to the medical inquiry. Further, the apparatus for suggesting a nutritional supplement may include the medical inquiry processing unit 1020 and/or the environment searching unit 1025.

In addition, the terminal 1000 of the customer may acquire the authentication information of the customer by reading the recording medium such as a magnetic card, an IC card, a flash memory, or the like on which the customer identification information including the customer ID is recorded instead of the input of the authentication information by using a keyboard.

In addition, the input-output apparatus 2000 may perform the authentication input of the customer by reading the recording medium such as a magnetic card, an IC card, a flash memory, or the like on which the customer identification information including the customer ID is recorded.

In addition, the medical inquiry processing unit 1020 may perform the medical inquiry to the terminal 1000 of the customer by sending the content of the medical inquiry item database 1210 to the terminal 1000 via the network 1001.

In addition, the medical inquiry processing unit 1020 may judge whether the medical inquiry is necessary in regard to a plurality of the medical inquiry items in the medical inquiry item database instead of the medical inquiry process shown in FIG. 14, display all of the medical message the medical inquiry items judged necessary to be inquired (S530) and acquire the response to the medical inquiry (S540). In this case, the medical inquiry processing unit 1020 may judge whether the medical inquiry item is not necessary due to the response to other medical inquiry item, when judging all of the medical inquiry items in the medical inquiry item database 1230.

Further, the medical inquiry processing unit 1020 may calculate the necessity degree of response, which a value indicating how much the response to the medical inquiry is necessary, based on various conditions of the medical inquiry designation for a step, the medical inquiry designation for a life goal, the medical inquiry interval, the medical inquiry designation for an insufficient nutrient and the correlation in the correlation database 1270, during judging whether the medical inquiry is necessary. In this case, the medical inquiry processing unit 1020 may perform the medical inquiry from the medical inquiry item of which the necessity degree of response is high in order. In addition, the medical inquiry processing unit 1020 may make up for the medical inquiry of the medical inquiry item without response of the customer by using the previous response to the medical inquiry of the customer held in the medical inquiry history database 1230, in case the customer stops the response to the medical inquiry.

In addition, the environment searching unit 1025 and the living environment database 1250 may process the living environment information such as the quality of water, the amount of ultraviolet ray, the precipitation, the noise and/or the like as well as the air pollution.

In addition, the total nutrients processing unit 1070 may adjust the nutrient requirement amount based on the correlation between the living environment and/or the life goal stored in the correlation database 1270 and the insufficient degree of nutrient. That is, the total nutrients processing unit 1070 may add the insufficient nutrient corresponding to the condition to the nutrient requirement amount, in case the customer satisfies the condition stored in the correlation database 1270.

In addition, the correlation processing unit 1040 may store a value indicating the amount of the insufficient nutrient into the correlation database 1270. The correlation processing unit 1040 may set the value indicating the amount of the insufficient nutrient to be the difference between the average values of the insufficient degree of nutrient either when the condition is satisfied or not. In this case, the total nutrients processing unit 1070 the amount of the insufficient nutrient corresponding to the condition to the nutrient requirement amount, if the customer satisfies the condition stored in the correlation database 1270.

In addition, the total nutrients processing unit 1070 may use the response to the medical inquiry of the medical inquiry item (the medical inquiry ID 4000 in FIG. 5) indicating whether the customer takes in the nutritional supplement suggested previously in regard to the total nutrient process (S600) shown in FIG. 15. That is, the total nutrients processing unit 1070 may increase the ingestion amount of nutrient corresponding to the countermeasure such as increasing the nutrient requirement amount, if the customer takes in the nutritional supplement suggested previously and the difference between the previous insufficient degree of nutrient stored in the medical inquiry history database 1230 and the present insufficient degree of nutrient by the response to the medical inquiry is smaller than a predetermined value.

In addition, the total nutrients processing unit 1070 may change the nutrient requirement amount based on the relation between the amount of the nutrient contained in the nutritional supplement prepared and the insufficient degree of nutrient by the medical inquiry after taking in the nutritional supplement while referring to the medical inquiry history database 1230 in the total nutrient process (S600) shown in FIG. 15.

In addition, the nutrient-for-purpose processing unit 1090, the personal information database 1200 and the life goal database 1260 may process various life goals in relation to nutrients including the diet, the improvement of athletic ability, the countermeasure against somberness of skin, the countermeasure against elasticity of skin, the countermeasure against brittleness, tendency toward peeling-off, fracture, fissure and/or the like of nails, the countermeasure against deformation or growth of nails, the countermeasure against irregular menstruation, the countermeasure against constipation, the countermeasure against diarrhea and/or the like as well as the improvement of the immunity, the countermeasure against dry skin and other skin problems shown in the exemplary embodiment above.

In addition, as the color of the nutritional supplement, the nutritional supplement suggesting unit 1130 and the personal information database 1200 may designate various colors, e.g., designate color randomly, according to the day on which the nutritional supplement is supposed to be taken in, different according to whether the nutritional supplement is a solid type or a liquid type and/or the like. Further, instead that the customer designates the colors held by the personal information database 1200 in advance, the medical inquiry processing unit 1020 or the preparation request inputting unit 1140 may allow the customer to input the color designation.

In addition, as the taste of the nutritional supplement, the nutritional supplement suggesting unit 1130 and the personal information database 1200 may designate various tastes, e.g., designate taste randomly, according to the day on which the nutritional supplement is supposed to be taken in, different according to whether the nutritional supplement is a solid type or a liquid type, allow the amount of condiment adjustable and/or the like. Further, instead that the customer designates the tastes held by the personal information database 1200 in advance, the medical inquiry processing unit 1020 or the preparation request inputting unit 1140 may allow the customer to input the taste designation.

In addition, as the smell of the nutritional supplement, the nutritional supplement suggesting unit 1130 and the personal information database 1200 may designate various smells, e.g., designate smell randomly, according to the day on which the nutritional supplement is supposed to be taken in, different according to whether the nutritional supplement is a solid type or a liquid type, allow the amount of flavoring adjustable and/or the like. Further, instead that the customer designates the smells held by the personal information database 1200 in advance, the medical inquiry processing unit 1020 or the preparation request inputting unit 1140 may allow the customer to input the smell designation.

In addition, as the package method of the nutritional supplement, the nutritional supplement suggesting unit 1130 and the personal information database 1200 may designate various package methods, e.g., designate the package method randomly, designate the method, piece, size, and/or the like of the package according to the day on which the nutritional supplement is supposed to be taken in, and/or the like. Further, instead that the customer designates package methods held by the personal information database 1200 in advance, the medical inquiry processing unit 1020 or the preparation request inputting unit 1140 may allow the customer to input the package method designation.

In addition, instead of the required amount and the upper limit ingestion amount per a day based on the data from Health and Welfare Ministry in Japan, the nutrient amount processing unit 1050 and the nutrient database 1240 may use certain standard of other country. Further, for example, the country name and/or the address may be registered in the nutrient database 1240, and the required amount and the upper limit ingestion amount designated by a plurality of countries may be held. In this case, the nutrient amount processing unit 1050 can determine the blend of the nutritional supplement based on the guidance designated by the country in which the customer resides by searching the nutrient database 1240 using the country of the customer.

As obvious from the description above, according to the present invention, it is possible to provide a blending system of a nutritional supplement capable of supporting nutrient ingestion corresponding to the constitution or various life goals of each person to be examined.

What is claimed is:

1. A blending system of a nutritional supplement for calculating nutrient requirement amount of a person to be examined from a response to a medical inquiry, said blending system being included in a server system for connecting to a client side terminal via a network, comprising:

a processing unit and a computer readable storage unit for storing a program, wherein when the program is executed by the processing unit, the program causes the blending system to provide:

a nutrient requirement amount calculating unit for acquiring said response of said person to be examined to said medical inquiry of a medical inquiry item from an outer part and calculating said nutrient requirement amount of said person to be examined based on a result of accumulating insufficient nutrients corresponding to each response to said medical inquiry;

a correlation processing unit for analyzing a correlation between said nutrient requirement amount judged by said nutrient requirement amount calculating device unit and a living environment or a life goal acquired from an outer part, in regard to a plurality of people to be examined; and a medical inquiry processing unit for designating a next medical inquiry item to perform said medical inquiry on said person to be examined by using a result of said analysis of said correlation, wherein said correlation processing unit sets a condition of the living environment or the life goal for which the correlation is to be analyzed, and calculates a correlation coefficient of the correlation between the condition and an insufficient amount of nutrient for each nutrient.

2. The blending system as claimed in claim 1, wherein said correlation processing unit judges whether the correlation coefficient corresponding to each nutrient is more than a predetermined value or not, and, when the correlation coefficient corresponding to at least one nutrient is more than the predetermined value, registers the correlation in a correlation database.

3. A blending system of a nutritional supplement for calculating nutrient requirement amount of a person to be examined from a response to a medical inquiry, said blending system being included in a server system for connecting to a client side terminal via a network, comprising:

a processing unit and a computer readable storage unit for storing a program, wherein when the program is executed by the processing unit, the program causes the blending system to provide:

a nutrient requirement amount calculating unit for acquiring said response of said person to be examined to said medical inquiry of a medical inquiry item from an outer part and calculating said nutrient requirement amount of said person to be examined based on a result of accumulating insufficient nutrients corresponding to each response to said medical inquiry;

a correlation processing unit for analyzing a correlation between said nutrient requirement amount judged by said nutrient requirement amount calculating device unit and a living environment or a life goal acquired from an outer part, in regard to a plurality of people to be examined;

a medical inquiry processing unit for designating a next medical inquiry item to perform said medical inquiry on said person to be examined by using a result of said analysis of said correlation; and a correlation database for storing a correlation ID, a condition corresponding to the correlation ID, and an insufficient nutrient, wherein said medical inquiry processing unit extracts an item in which data relating to the customer matches the condition registered in said correlation database and judges that the insufficient nutrient of the item is insufficient to the person to be examined.

4. An apparatus for calculating nutrient requirement amount of a person to be examined from a response to a medical inquiry including:

a processing unit and a computer readable storage medium storing thereon a program, said program causing the apparatus to function as:

a nutrient requirement amount calculating section for acquiring said response of said person to be examined to said medical inquiry of a medical inquiry item from an outer part and calculating said nutrient requirement amount of said person to be examined based on a result of accumulating insufficient nutrients corresponding to each response to said medical inquiry;

a correlation processing section for analyzing a correlation between said nutrient requirement amount calculated by said nutrient requirement amount calculating section and a living environment or a life goal acquired from an outer part, in regard to a plurality of people to be examined; and a medical inquiry processing section for designating a next medical inquiry item to perform said medical inquiry on said person to be examined by using a result of said analysis of said correlation, wherein said correlation processing section sets a condition of the living environment or the life goal for which the correlation is to be analyzed, and calculates a correlation coefficient of the correlation between the condition and an insufficient amount of nutrient for each nutrient.

5. The apparatus for calculating nutrient requirement amount including the processing unit and the computer readable storage medium as claimed in claim 4, wherein said correlation processing section judges whether the correlation coefficient corresponding to each nutrient is more than a predetermined value or not, and, when the correlation coefficient corresponding to at least one nutrient is more than the predetermined value, registers the correlation in a correlation database.

6. An apparatus for calculating nutrient requirement amount of a person to be examined from a response to a medical inquiry including:

a processing unit and a computer readable storage medium storing thereon a program, said program causing the apparatus to function as:

a nutrient requirement amount calculating section for acquiring said response of said person to be examined to said medical inquiry of a medical inquiry item from an outer part and calculating said nutrient requirement amount of said person to be examined based on a result of accumulating insufficient nutrients corresponding to each response to said medical inquiry;

a correlation processing section for analyzing a correlation between said nutrient requirement amount calculated by said nutrient requirement amount calculating section and a living environment or a life goal acquired from an outer part, in regard to a plurality of people to be examined;

a medical inquiry processing section for designating a next medical inquiry item to perform said medical inquiry on said person to be examined by using a result of said analysis of said correlation; and a correlation database for storing a correlation ID, a condition corresponding to the correlation ID, and an insufficient nutrient, wherein said medical inquiry processing section extracts an item in which data relating to the customer matches the condition registered in said correlation database and judges that the insufficient nutrient of the item is insufficient to the person to be examined.

7. A computer readable storage medium storing thereon a program for an apparatus for calculating nutrient requirement amount of a person to be examined from a response to a medical inquiry including, said program causing the apparatus to perform:

acquiring said response of said person to be examined to said medical inquiry of a medical inquiry item from an outer part and calculating said nutrient requirement amount of said person to be examined based on a result of accumulating insufficient nutrients corresponding to each response to said medical inquiry;

analyzing a correlation between said nutrient requirement amount calculated by said nutrient requirement amount calculating section and a living environment or a life goal acquired from an outer part, in regard to a plurality of people to be examined;

designating a next medical inquiry item to perform said medical inquiry on said person to be examined by using a result of said analysis of said correlation; and storing a correlation ID, a condition corresponding to the correlation ID, and an insufficient nutrient, wherein the step of analyzing further sets a condition of the living environment or the life goal for which the correlation is to be analyzed, and calculates a correlation coefficient of the correlation between the condition and an insufficient amount of nutrient for each nutrient, when the program is run on the apparatus.

8. A computer readable storage medium storing thereon a program for an apparatus for calculating nutrient requirement amount of a person to be examined from a response to a medical inquiry including, said program causing the apparatus to perform:

acquiring said response of said person to be examined to said medical inquiry of a medical inquiry item from an outer part and calculating said nutrient requirement amount of said person to be examined based on a result of accumulating insufficient nutrients corresponding to each response to said medical inquiry;

analyzing a correlation between said nutrient requirement amount calculated by said nutrient requirement amount calculating section and a living environment or a life goal acquired from an outer part, in regard to a plurality of people to be examined;

designating a next medical inquiry item to perform said medical inquiry on said person to be examined by using a result of said analysis of said correlation; and storing a correlation ID, a condition corresponding to the correlation ID, and an insufficient nutrient, wherein the step of designating further extracts an item in which data relating to the customer matches the condition registered in said correlation database and judges that the insufficient nutrient of the item is insufficient to the person to be examined, when the program is run on the apparatus.

* * * * *